(12) United States Patent
Naparstek et al.

(10) Patent No.: US 8,642,041 B2
(45) Date of Patent: Feb. 4, 2014

(54) ADENYLYL CYCLASE-ASSOCIATED PROTEIN (CAP1) AND USES THEREOF AS A TARGET FOR IMMUNO-MODULATION

(75) Inventors: Yaakov Naparstek, Jerusalem (IL); Eli Moallem, Jersusalem (IL)

(73) Assignee: Protab Ltd., Jerusalem (IL)

( * ) Notice: Subject to any disclaimer, the term of this patent is extended or adjusted under 35 U.S.C. 154(b) by 0 days.

(21) Appl. No.: 13/257,633

(22) PCT Filed: Mar. 21, 2010

(86) PCT No.: PCT/IL2010/000231
§ 371 (c)(1),
(2), (4) Date: Sep. 20, 2011

(87) PCT Pub. No.: WO2010/113148
PCT Pub. Date: Oct. 7, 2010

(65) Prior Publication Data
US 2012/0014973 A1    Jan. 19, 2012

Related U.S. Application Data

(60) Provisional application No. 61/164,489, filed on Mar. 30, 2009.

(51) Int. Cl.
*A61K 39/00* (2006.01)

(52) U.S. Cl.
USPC ............... 424/173.1; 424/139.1; 424/146.1; 424/810; 514/16.6; 514/18.7; 530/387.1; 530/388.26; 530/388.7; 530/868

(58) Field of Classification Search
None
See application file for complete search history.

(56) References Cited

U.S. PATENT DOCUMENTS

| | | | |
|---|---|---|---|
| 5,698,195 A * | 12/1997 | Le et al. ................... | 424/133.1 |
| 6,770,281 B2 * | 8/2004 | Naparstek et al. .......... | 424/190.1 |
| 6,846,486 B1 * | 1/2005 | Skurkovich et al. ........ | 424/130.1 |
| 7,488,476 B2 * | 2/2009 | Naparstek et al. .......... | 424/139.1 |
| 8,158,125 B2 * | 4/2012 | Naparstek et al. .......... | 424/139.1 |
| 2002/0150586 A1 | 10/2002 | Naparstek | |
| 2005/0123535 A1 * | 6/2005 | Naparstek et al. .......... | 424/131.1 |

FOREIGN PATENT DOCUMENTS

| WO | 2004/034062 A2 | 4/2004 |
|---|---|---|
| WO | WO 2004034062 A2 * | 4/2004 |
| WO | 2006/082406 A2 | 8/2006 |
| WO | 2009/024986 A2 | 2/2009 |

OTHER PUBLICATIONS

Zhou et al., Immunity. May 2009;30(5):646-55.*
Lloyd et al., Immunity. Sep. 18, 2009;31(3):438-49.*
Blaydes et al., Methods Mol Biol. 2000;99:177-89.*
Czernik et al., Methods Enzymol. 1991;201:264-83.*
Holoshitz, J. et al. Science 219:56-58 (1983).
Lider, O. et al. Proc. Natl. Acad. Sci. 84:4577-4580 (1987).
Moudgil, K. et al. J. Exp. Med. 185:1307-1316 (1997).
Ulmansky, R., and Y. Naparstek, Eur. J. Immunol. 25:952-957 (1995).
Ulmansky, R. and Y. Naparstek, J. Immunol. 168: 6463-6469 (2002).
GeneBank Accession No. NP_001099000.1 (Aug. 14, 2011).
GeneBank Accession No. CAG33690.1 (Oct. 16, 2008).
Wahl et al., J. Nucl. Med. 24:316-325 (1983).
Prakken B. et al., Springer Semin. Immunopathol. 25: 7-63 (2003).
Lee, K. et al. Gene. Anal. Technol. 5:22-31 (1988).
Ma, W. et al. J. Biol. Chem. 276:13664-13674 (2001).
Platzer, C. et al. Eur. J. Immunol. 29:3098-3104 (1999).
Kase, H. et al. Bioch. Biophys. Res. Com. 142:436-440 (1987).
Cauwe Benedict et al., Experimental Cell Research (2008) 314(15):2739-2749.
Dumont, Expert Opin. Ther. Patents (2002) 12(3):341-367.
Hubberstey et al., FASEB Journal (2002), 16:487-499.
Naparstek Y. et al., Autoimmunity Reviews (2004) 3(7-8):588-589.
Yamazaki Ken et al., Laboratory Investigation; A Journal of Technical Methods and Pathology (2009) 89(4):425-432.
Haraguchi Soichi et al., Immunologic Research (2008) 41(1):46-55.
Dhafer et al.; "IL-10 is critical for Th2 responses in a murine model of allergic dermatitis"; The Journal of Clinical investigation vol. 112(7):1058-1065 (2003) 9 pages.
Virginie Barbarin et al.; "Pulmonary overexpression of IL-10 augments lung fibrosis and Th2 responses induced by silica particles"; Am. J. Physiol Lung Cell Mol Physiol 288: L841-L848, (2005) 9 pages.
Makela et al.; "The Failure of Interleukin-1-deficient Mice to Develop Airway Hyperresponsiveness Is Overcome by Respiratory Syncytial Virus Infection in Allergen-sensitized/challenged Mice"; Am. J. Resp. Crit. Care Med vol. 165:824-831 (2002) 8 pages.
Zhang et al.; "Th2 Cytokine Levels Distort the Association IL-10 and IFN-y with Allergic Phenotypes"; ISRN Allergy Article ID 405813 (2011) 6 pages.

* cited by examiner

*Primary Examiner* — Michael Szperka
(74) *Attorney, Agent, or Firm* — Browdy and Neimark, PLLC

(57) ABSTRACT

The present invention relates to the use of Adenylyl Cyclase-Associated Protein (CAP1) as a target for immuno-modulation. More specifically, the invention relates to the use of compounds that interact and bind CAP1, specifically, anti-CAP1 antibodies, and/or to CAP1 molecule or any fragments thereof, for the treatment of immune-related disorders by modulation of the Th1/Th2 balance. The invention further provides screening method for immuno-modulatory compounds that interact with CAP1.

5 Claims, 29 Drawing Sheets

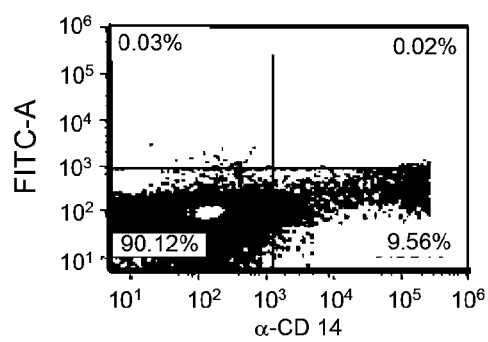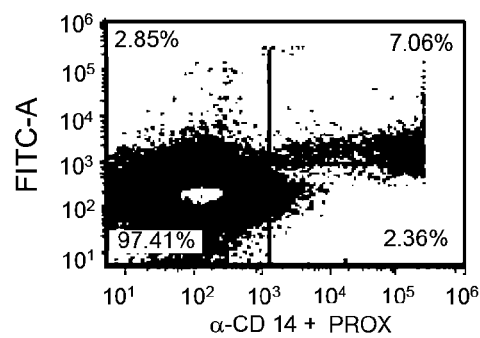
Fig. 5A　　　　　　　　Fig. 5B
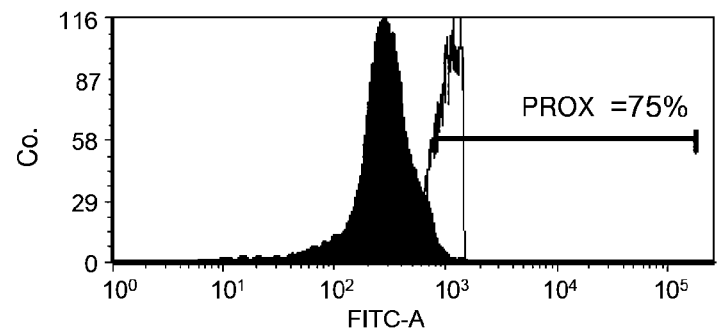
Fig. 5C

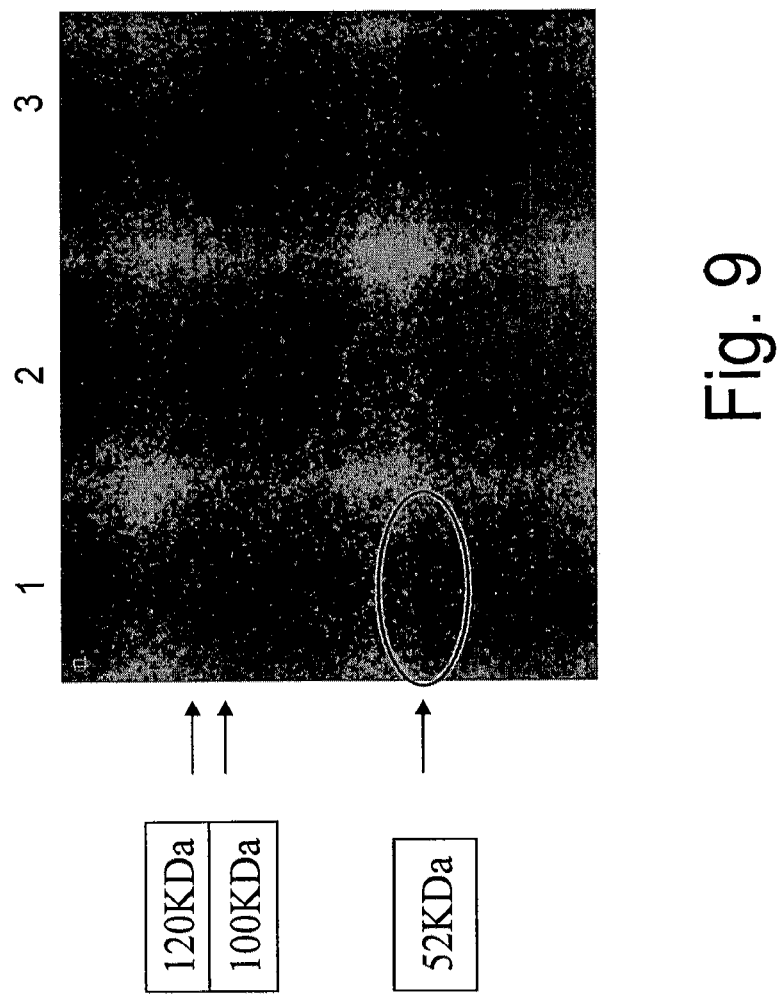

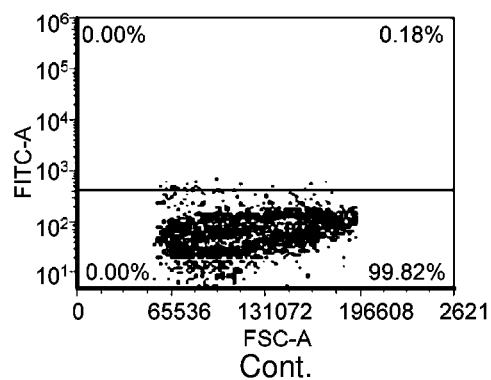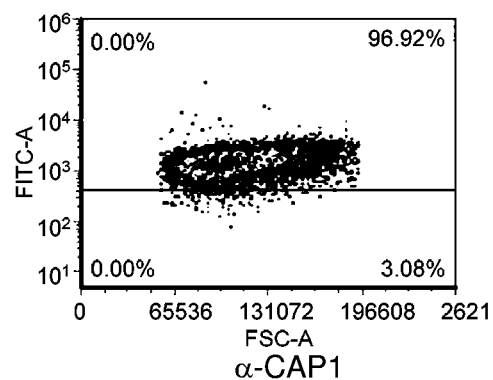
Fig. 16A    Fig. 16B
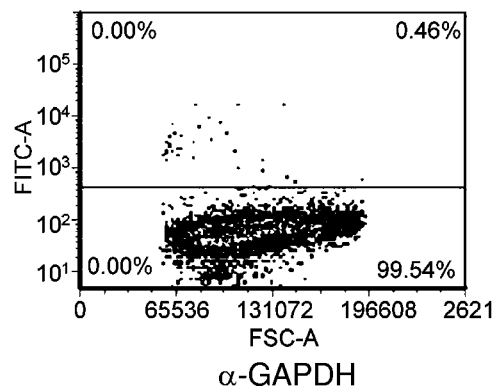
Fig. 16C

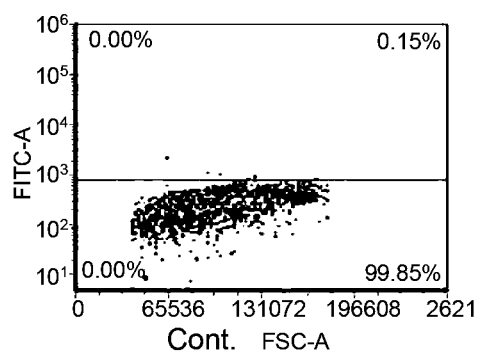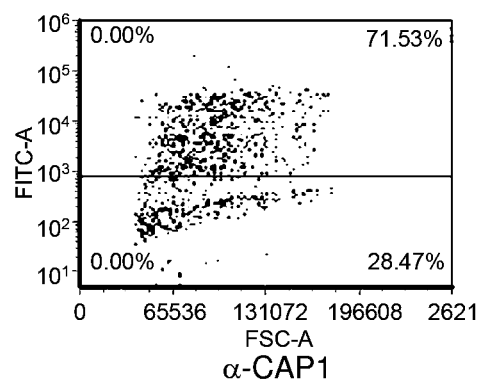
Fig. 17A  Fig. 17B
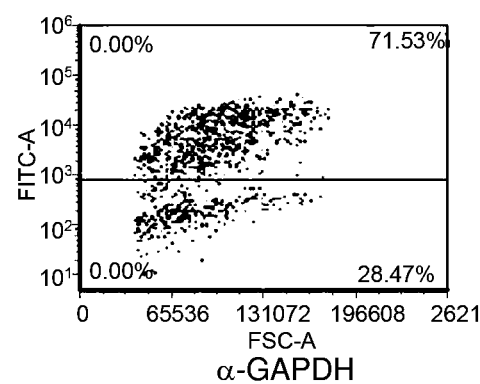
Fig. 17C

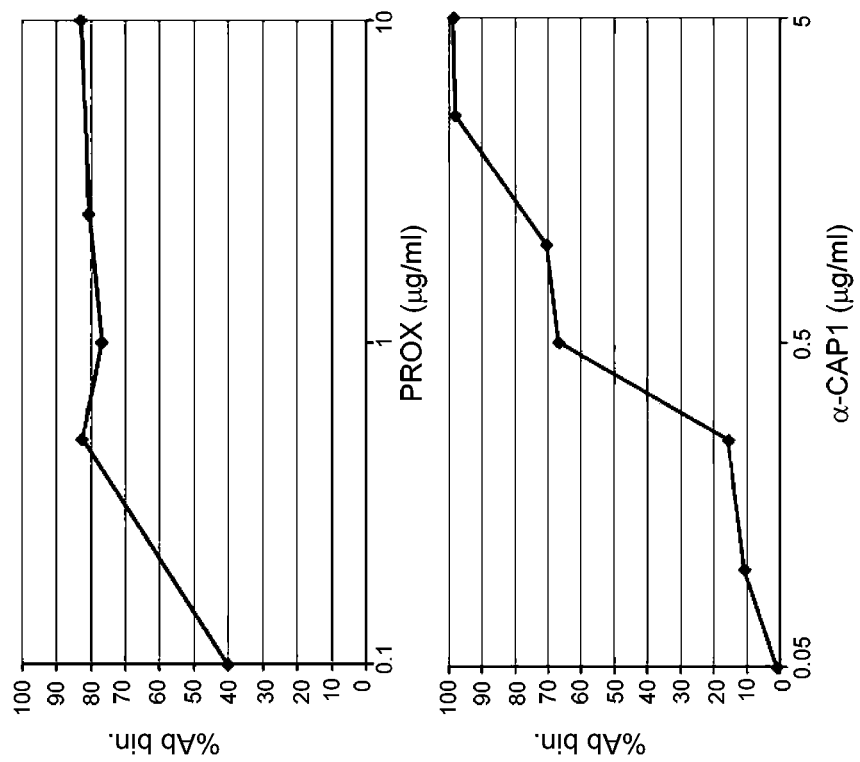

NCBI Reference Sequence: NP_001099000.1 adenylyl cyclase-associated protein 1 [Homo sapiens]

```
LOCUS       NP_001099000     475 aa    linear   PRI 14-MAR-2010
DEFINITION  adenylyl cyclase-associated protein 1 [Homo sapiens].
ACCESSION   NP_001099000
VERSION     NP_001099000.1  GI:157649073
DBSOURCE    REFSEQ: accession NM_001105530.1
ORGANISM    Homo sapiens
Eukaryota; Metazoa; Chordata; Craniata; Vertebrata; Euteleostomi;
Mammalia; Eutheria; Euarchontoglires; Primates; Haplorrhini;
Catarrhini; Hominidae; Homo.
REFERENCE   1  (residues 1 to 475)
AUTHORS Yamazaki,K., Takamura,M., Masugi,Y., Mori,T., Du,W., Hibi,T.,
Hiraoka,N., Ohta,T., Ohki,M., Hirohashi,S. and Sakamoto,M.
TITLE   Adenylate cyclase-associated protein 1 overexpressed in
pancreatic cancers is involved in cancer cell motility
JOURNAL     Lab. Invest. 89 (4), 425-432 (2009)
PUBMED      19188911
FEATURES             Location/Qualifiers
     source          1..475
                     /organism="Homo sapiens"
                     /db_xref="taxon:9606"
                     /chromosome="1"
                     /map="1p34.2"
     Protein         1..475
                     /product="adenylyl cyclase-associated protein 1"
                     /note="CAP 1"
                     /calculated_mol_wt=51542
     CDS             1..475
                     /gene="CAP1"
                     /gene_synonym="CAP; CAP1-PEN"
                     /coded_by="NM_001105530.1:212..1639"
                     /db_xref="CCDS:CCDS41309.1"
                     /db_xref="GeneID:10487"
                     /db_xref="HGNC:20040"
```

Fig. 30

```
ORIGIN
  1 madmqnlver leravgrlea vshtsdmhrg yadspskaga apyvqafdsl lagpvaeylk
 61 iskeiggdvq khaemvhtgl klerallvta sqcqqpaenk lsdllapise qikevitfre
121 knrgsklfnh lsavsesiqa lgwvamapkp gpyvkemnda amfytnrvlk eykdvdkkhv
181 dwvkaylsiw telqayikef httglawskt gpvakelsgl psgpsagsgp pppppgpppp
241 pvstssgsde sasrsalfaq inqgesitha lkhvsddmkt hknpalkaqs gpvrsgpkpf
301 sapkpqtsps pkratkkepa vlelegkkwr venqenvsnl viedtelkqv ayiykcvntt
361 lqikgkinsi tvdnckklgl vfddvvgive iinskdvkvq vmgkvptisi nktdgchayl
421 sknsldceiv sakssemnvl ipteggdfne fpvpeqfktl wngqklvttv teiag
//
```

Fig. 30 (cont.)

ADENYLYL CYCLASE-ASSOCIATED PROTEIN (CAP1) AND USES THEREOF AS A TARGET FOR IMMUNO-MODULATION

REFERENCE TO CO-PENDING APPLICATIONS

Priority is claimed as a 371 of international application number PCT/IL2010/000231, filed on Mar. 21, 2010; which claims priority as a U.S. Provisional patent application Ser. No. 61/164,489, filed on Mar. 30, 2009.

FIELD OF THE INVENTION

The present invention relates to the use of Adenylyl Cyclase-Associated Protein (CAP1) as a target for immuno-modulation. More specifically, the invention relates to the use of CAP1 or compounds that interact with CAP1 in compositions and methods for the treatment of immune disorders.

BACKGROUND OF THE INVENTION

All publications mentioned throughout this application are fully incorporated herein by reference, including all references cited therein.

The 65-kDa heat shock protein (HSP65) of the *Mycobacterium Tuberculosis* plays a significant role in the pathogenesis of autoimmune arthritis. Its effect is well exemplified in the experimental model of adjuvant arthritis (AA). AA can be induced in susceptible, inbred strains of rats such as Lewis or Wistar, by intracutaneous inoculation of heat killed mycobacteria suspended in Freunds adjuvant. AA can be passively transferred by a T-cell clone reactive to residues 180-188 of the HSP65 [Holoshitz, J. et al. Science 219:56-58 (1983)].

Evidence has been reported that protection from disease may be due to cellular responses to HSP65 [Lider, O. et al. Proc. Natl. Acad. Sci. 84:4577-4580 (1987); Moudgil, K. et al. J. Exp. Med. 185:1307-1316 (1997)], suggesting that this protein contains different epitopes which participate in both pathogenesis and acquisition of resistance. The inventors have previously shown that resistance to AA can also be conferred by antibodies against HSP65 and can be passively transferred by intravenous infusion of immunoglobulins from arthritis-resistant strains to arthritis-susceptible rats [Ulmansky, R., and Y. Naparstek, Eur. J. Immunol. 25:952-957 (1995)]. Further analysis defined the epitope specificity of the anti-HSP protective antibodies to amino-acid residues 31-46, designated as peptide-6 (also denoted by SEQ ID NO. 1) [Ulmansky, R. and Y. Naparstek, J. Immunol. 168: 6463-6469 (2002)]. Vaccination of Lewis rats with this peptide resulted in the production of antibodies against the whole molecule as well as resistance to disease induction.

The inventors have previously shown that polyclonal antibodies against peptide-6 stimulate IL-10 production by peripheral blood mononuclear cells (PBMCs) [Ulmansky (2002) ibid.]. The anti-inflammatory cytokine IL-10 plays an important role in innate immunity mostly due to its inhibitory effects, which allow suppression of inflammatory responses. Monoclonal, as well as chimeric and humanized anti-peptide-6 antibodies (Proximab) generated by the inventors were shown to retain this protective effect by binding to PBMCs and stimulating IL-10 secretion from the cells.

The inventors have now also shown that antibodies directed against peptide-6 interact not only with peptide-6, but moreover, they cross react directly with a surface ligand on monocytes, and this interaction is the key for comprehension of the mechanism of action of these antibodies. Following binding of the anti-peptide-6 antibodies to monocytes, there is activation of a signal transduction pathway that leads to an increase in production and secretion of cytokines, specifically IL-10 that as an anti-inflammatory cytokine, attenuates and inhibits inflammatory processes, thereby leading to amelioration and treatment of an inflammatory disorder. This tilts the balance between pro-inflammatory Th1 cytokines, such as tumor necrosis factor alpha (TNF-alpha), and anti-inflammatory Th2 cytokines, such as IL-10. Modulation of the Th1/Th2 balance towards a Th2 anti-inflammatory response by the anti-peptide-6 antibodies has been therefore shown by the present inventors as applicable in the treatment of inflammatory disorders.

As shown by the present invention, the cellular target of the anti-peptide-6 antibodies is the CAP1 protein. Cyclase-associated proteins (CAPs) are evolutionarily conserved proteins which function in regulation of the actin cytoskeleton and in signal transduction pathways. Mammals have two CAP genes, encoding the related CAP1 and CAP2. CAP1 shows a broad tissue distribution, whereas CAP2 is significantly expressed only in brain, heart and skeletal muscle, and skin. The cDNA of human CAP1 was identified, cloned and shown to encode a 475 amino acid protein that is homologous to the yeast CAP proteins.

The original CAP was isolated as a component of the *Saccharomyces cerevisiae* adenylyl cyclase complex that serves as an effector of Ras/cyclic AMP pathway during nutritional signaling. CAPs are multifunctional molecules that contain domains involved in several functions. The NH2 terminus is necessary and sufficient for cellular responsiveness to activated RAS proteins, while the COOH terminus is required for normal cellular morphology and growth control. Genetic studies in yeast have implicated CAPs in vesicle trafficking and endocytosis. CAPs play a developmental role in multi-cellular organisms, and studies of Drosophila have illuminated the importance of the actin cytoskeleton during eye development and in establishing oocyte polarity.

Human CAP1 is a component of actin-cofilin complex. Human CAP is a bifunctional protein with an N-terminal domain that binds to Ras-responsive adenylyl cyclase and a C-terminal domain that inhibits actin polymerization. CAP1 and its C-terminal domain were observed to facilitate filament elongation at the barbed end and to stimulate ADP-ATP exchange on globular (G) (monomeric) actin subunits, a process that regenerates easily polymerizable G-actin.

The direct interaction of the anti-peptide-6 antibodies with the CAP1 molecule that was first shown by the invention as leading to induction of IL-10 expression, probably through cAMP dependent protein kinase, reflect the involvement of CAP1 as a key element in this novel pathway. These findings establish the possibility of using the CAP1 as a target for immuno-modulation of this particular pathway. Moreover, anti-CAP1 antibodies were shown to induce IL-10 expression, demonstrating the feasibility of using a CAP1 binding compound as an immuno-modulator.

It is therefore an object of the invention to provide the use of a compound that specifically binds and interacts with CAP1, in methods and compositions for the treatment of immune-related disorders.

Another object of the invention is to provide the use of CAP1 and any fragments thereof, as an immuno-modulating compound.

In yet another object, the invention provides the use of CAP1 in a screening method for identification of immuno-modulating compounds. Such compounds may be useful in modulating the Th1/Th2 balance in a subject suffering of an immune-related disorder.

These and other objects of the invention will become apparent as the description proceeds.

SUMMARY OF THE INVENTION

In a first aspect, the invention relates to a composition for the modulation of the Th1/Th2 balance in a subject in need thereof. The composition of the invention comprises as an active ingredient an immuno-modulatory effective amount of at least one of: (a) a compound that interacts with Adenylyl Cyclase-Associated Protein (CAP1); and/or (b) CAP1 or any fragment, variant, derivative, homologue and mutant thereof; or any combination thereof. The composition of the invention optionally further comprises a pharmaceutically acceptable carrier, excipient or diluent.

According to one specific embodiment, the composition of the invention comprises as an active ingredient a therapeutically effective amount of an anti-CAP1 antibody.

The invention also provides a therapeutic composition for treating, preventing, ameliorating or delaying the onset of an immune-related disorder by modulating the Th1/Th2 balance in a subject in need thereof. The therapeutic composition of the invention comprises as an active ingredient an immuno-modulatory effective amount of at least one of: (a) a compound that interacts with Adenylyl Cyclase-Associated Protein (CAP1); and/or (b) CAP1 or any fragment, variant, derivative, homologue and mutant thereof; or any combination thereof. The composition optionally further comprises a pharmaceutically acceptable carrier, excipient or diluent.

A further aspect of the invention relates to a method for treating, preventing, ameliorating or delaying the onset of an immune-related disorder in a subject in need thereof. The method of the invention involves the step of administering to the subject a therapeutically effective amount of at least one of: (a) a compound that interacts with Adenylyl Cyclase-Associated Protein (CAP1); and/or (b) of CAP1, or any fragment, variant, derivative, homologue and mutant thereof; or any combination thereof or any composition comprising the same.

In another aspect, the invention relates to the use of a therapeutically effective amount of at least one of: (a) a compound that interacts with Adenylyl Cyclase-Associated Protein (CAP1); and/or (b) of CAP1 or any fragment, variant, derivative, homologue and mutant thereof, or any combination thereof, in the preparation of a composition for the treatment of immune-related disorders.

In a fifth aspect, the invention provides Adenylyl Cyclase-Associated Protein (CAP1) or any fragment, variant, derivative, homologue and mutant thereof, that modulates the balance between Th1/Th2 in a subject in need thereof, for use in treating, preventing, ameliorating or delaying the onset of an immune-related disorder.

The invention also provides an anti-CAP1-antibody that specifically recognizes and binds CAP1, thereby modulating the balance between Th1/Th2 towards the Th2 anti-inflammatory response in a subject in need thereof, for use in treating, preventing, ameliorating or delaying the onset of an immune-related disorder.

Furthermore, the invention relates to a screening method for an immuno-modulating compound which modulates the Th1/Th2 cell balance in a subject in need thereof. The method of the invention comprises the steps of (a) obtaining a candidate compound which binds to CAP1 or to any fragment, variant, derivative, homologue and mutant thereof;

(b) determining the effect of the compound selected in step (a), on modulation of an anti-inflammatory cytokine expression.

Whereby modulation of an anti-inflammatory or a pro-inflammatory cytokine expression by the candidate compound is indicative of the ability of the compound to modulate the Th1/Th2 balance in the subject.

The invention also provides an immuno-modulatory compound which interacts with CAP1 and thereby modulates the Th1/Th2 cell balance in a subject in need thereof, wherein the compound is identified by the screening method according to the invention.

Finally, the invention relates to a pharmaceutical unit dosage form comprising as an active ingredient a therapeutically effective amount of at least one of: (a) a compound that interacts with Adenylyl Cyclase-Associated Protein (CAP1); and/or (b) of CAP1 or any fragment, variant, derivative, homologue and mutant thereof, or any combination thereof, for the preparation of a medicament effective in treating, preventing, ameliorating or delaying the onset of an immune-related disorder. The dosage form of the invention optionally further comprises a pharmaceutically acceptable carrier, excipient or diluent.

Further aspects of the invention will become apparent by the hand of the following drawings.

Murine Anti-Peptide-6 Antibody Induces IL-10 Secretion In Vitro

Naïve human monocytes were incubated (24 h, 37° C., 5% $CO_2$) in RPMI with murine anti-peptide-6 monoclonal antibody (mAb), and IL-10 secretion to the medium was measured by ELISA. Untreated cells served as a control. Abbreviations: Mon. ce. (mononuclear cells); α-pep 6 (anti-peptide-6 (SEQ ID NO. 1) antibody) Un. (units); IL-10 (Interleukin 10).

FIG. 2A-2B

Anti-Peptide-6 Antibodies Induce Transient Upregulation of IL-10 Transcription

Figures 2A, 2B:
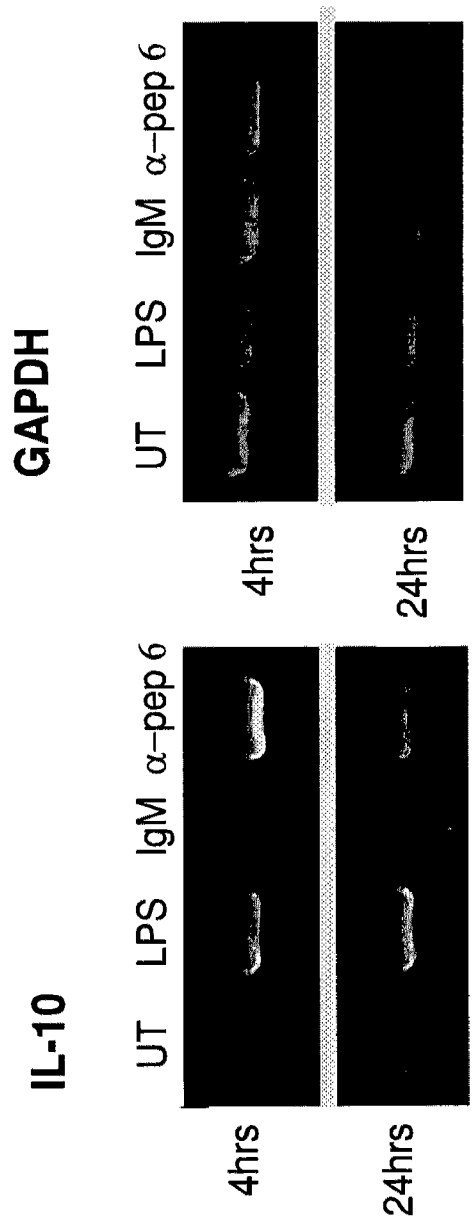

Human monocyte cells (PBMC) were incubated with either the murine B24 anti-peptide-6 monoclonal antibody, total naïve Lewis IgM antibodies as a negative control or lipopolysaccharide (LPS) as a positive control. The cells were harvested after 4 and 24 hours following exposure to LPS, total naïve Lewis IgM control or B24, and extracted mRNA was assayed using RT-PCR (FIG. 2A). Both LPS and the anti-peptide-6 antibody induced an increase in IL-10 mRNA four hours post-exposure, compared to the untreated and naïve Lewis IgM-treated cells. However, the expression level in cells treated with anti-peptide-6 were reduced after 24 hours of incubation with the antibody, contrary to the LPS-treated cells, in which the mRNA level remained constant 24 hours post-exposure. GAPDH cDNAs were used as control for equal loading (FIG. 2B).

Abbreviations: UT. (untreated); LPS (lipopolysaccharide); IgM (naïve Lewis IgM antibodies); α-pep-6 (anti-peptide-6 antibody), hr. (hour).

FIG. 3

Proximab Induces IL-10 Expression and Alleviates Adjuvant Arthritis In Vivo

Six to eight week old female inbred Lewis rats were injected intradermally at the base of the tail with 1 mg of MT H37Ra in CFA. Animals were treated with either Phosphate Buffer Solution (PBS negative control), steroids or Proximab. Severity of arthritis was evaluated by adjuvant arthritis (AA) scoring. Arthritis was assessed every other day by a blinded observer as follows: 0, no arthritis; 1, redness of the joint; 2, redness and swelling of the joint. The ankle and tarsal-metatarsal joints of each paw were scored. A maximum score of 16 can be obtained. IL-10 levels were measured by ELISA. Results are the mean±SE of 2 rats per group. Abbreviations: Cont. (PBS negative control); PROX (Proximab antibody); STR (steroids); AA Sc. (adjuvant arthritis score); pg/ml (picogram/mililiter).

FIG. 4A-4D

Chimeric Anti-Peptide-6 Antibody Binds to Isolated CD14+ Human Monocyte PBMCs

Figure 4A:
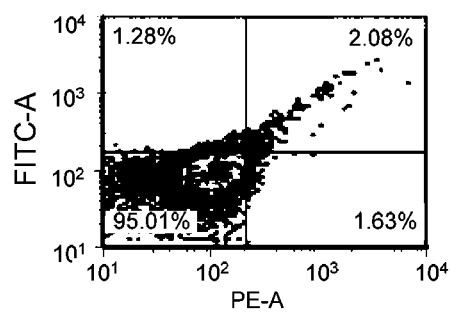
Figure 4B:
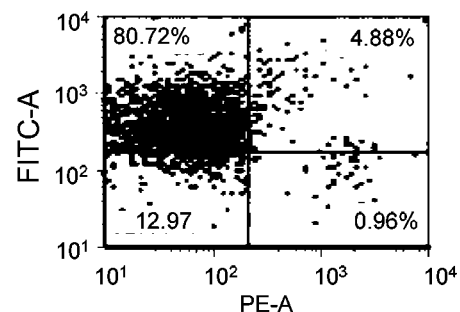
Figure 4C:
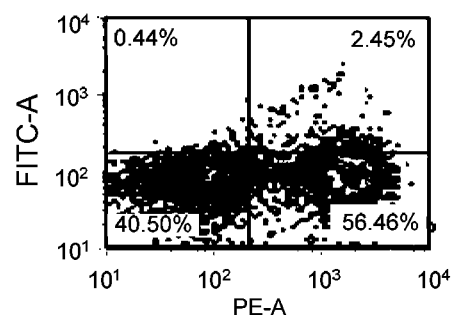
Figure 4D:
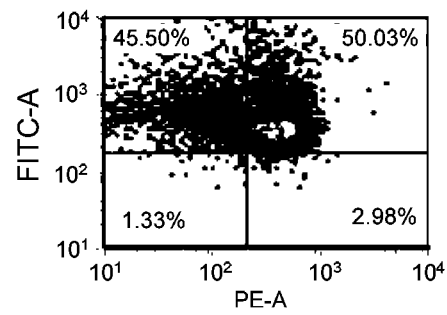

CD14+ cells were isolated from human PBMCs with CD14 magnetic beads and stained with either a FITC labeled chimeric anti-peptide-6 antibody (FIG. 4B), or anti-human CD14-PE (FIG. 4C), or both (FIG. 4D). Unstained cells (FIG. 4A) were used as a negative control. The cells were analyzed by FACS for the binding of the antibodies. As shown by FIG. 4D, most of the cells which were CD14 positive were positive for chimeric anti-peptide-6 as well.

FIG. 5A-5C

Proximab Binds Human CD14+ PBMCs

Human PBMCs were isolated from a healthy donor and separated on a Ficoll gradient. The isolated cells were stained with either anti CD14-APC conjugated antibodies (FIG. 5A) or with both FITC-labeled Proximab and APC conjugated-anti-CD14 antibodies (FIG. 5B). The percent of cells out of the CD14+ population that were stained with FITC is depicted in FIG. 5C (without Proximab—black, with Proximab—gray). Abbreviations: α-CD14 (anti-CD14 antibody); PROX (anti-peptide-6 humanized antibody).

FIG. 6A-6B

Figures 6A, 6B:
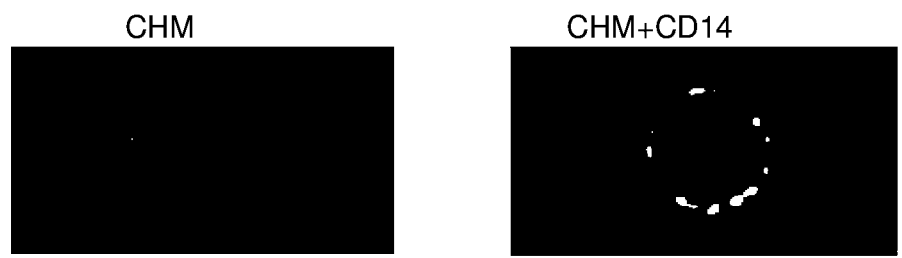

Chimeric Anti-Peptide-6 Antibody and Anti-CD14 Antibodies Bind to Monocyte Membranes CD14+ Mono Mac 6 (MM6) cells were incubated with chimeric anti-peptide-6 antibodies (CHM antibodies), and then stained with anti-human IgG-FITC conjugated antibodies alone (FIG. 6A) or together with mouse-anti human CD14-APC (FIG. 6B). After staining, cells were fixed, placed on slides and viewed under a confocal microscope. The ligand of the CHM antibody is located on the membrane surface of CD14 positive cells. Abbreviations: CHM (chimeric anti-peptide-6 antibody); CD14 (anti-CD14 antibody).

FIG. 7

Humanized Anti-Peptide-6 Antibody does not Bind Via Human Monocyte Fc-Receptors

MM6 cells were either untreated or pre-incubated with non-labeled humanized anti-peptide-6 antibody variant VK3 or with antibodies to CD32 and CD64, then treated with FITC-VK3 and assayed by FACS for bound FITC-VK3. The FITC-VK3 bound to 30% of the cells (left bar). Pre-incubation with the non-fluorescent VK3 antibody completely abolished VK3-FITC binding (middle bar), but pre-incubation with antibodies against both Fc receptors had no effect (right bar). Abbreviations: VK3 (FITC conjugated humanized anti-peptide-6 antibody); PRI(VK3)+VK3 (pre-incubation with non-labeled VK3 followed by FITC VK3); PRI(CD32+CD64)+VK3 (pre-incubation with anti-CD32 and anti-CD64 followed by FITC VK3); bo. Ce. (bound cells).

FIG. 8A-8B

Rat Anti-Peptide-6 Antibodies Bind THP-1 Cells

Figure 8B:
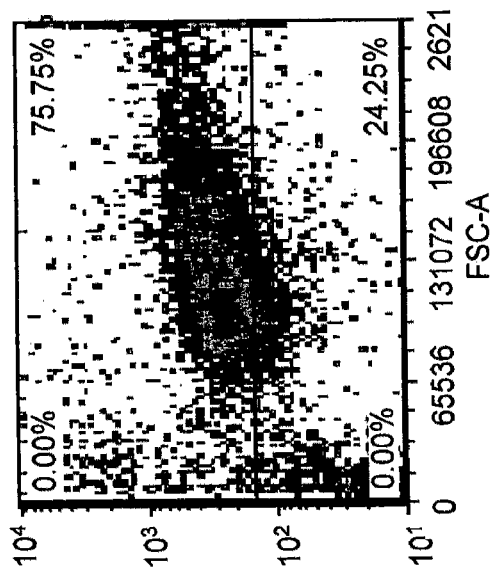

Human promonocytic THP-1 cells were incubated with rat anti-peptide-6 monoclonal antibody (B24) followed by FITC staining, and then subjected to FACS analysis. Cells incubated only with the secondary antibody (FITC-goat anti-rat) served as control (FIG. 8A). 75% of the cells incubated with rat anti-peptide-6 monoclonal antibody bound to the B24 antibodies (FIG. 8B).

FIG. 9

The Monoclonal Anti-Peptide-6 Target is a Monocyte Hydrophilic Membrane Protein

Hydrophilic membrane proteins, hydrophobic membrane proteins and cytoplasmic proteins were isolated from THP-1 cells, and subjected to Western blot analysis, using the murine B24 monoclonal anti-peptide-6 antibody (data not shown). Control blots were blotted with total rat immunoglobulins or medium only. Lane 1—hydrophilic membrane proteins; lane 2—hydrophobic membrane proteins, lane 3—cytoplasmic proteins. As demonstrated, the B24 antibody bound three fractions of the hydrophilic membrane proteins: 52, 100 and 120 KDa. No binding was detected in the negative control blots. Abbreviations: KDa (kilo Dalton).

FIG. 10

Analysis of the Anti-Peptide-6 Protein Target

The hydrophilic membrane fraction of THP-1 cells was loaded on affinity columns containing murine monoclonal anti-peptide-6 antibodies bound to Sepharose beads. The bound proteins were eluted and loaded on SDS-PAGE, followed by Coomassie Blue staining. Lane 2 represents affinity chromatography on a rat anti-peptide-6 column and lane 4 represents affinity chromatography on a mouse anti-peptide-6 column. Lanes 1 and 6 include the marker. Two doublet bands of approximately 40 and 50 KDa can be seen in lanes 2 and 4. The bands were cut out and analyzed by mass-spectrometry. The 52 KDa band was sequenced and found to contain Adenylyl Cyclase-Associated Protein (CAP1).

FIG. 11

Anti-Peptide-6 Binds to a 52 kDa Membrane Protein as Well as Binding to MT-HSP65

THP-1 hydrophilic membrane proteins eluted from anti-peptide-6 affinity chromatography column and MT-HSP65 were loaded on SDS-PAGE and subjected to Western blot analysis, using the rat anti-peptide-6 antibody (B24). Two different bands were detected: a 52 KDa protein, observed in the lane loaded with the eluted proteins obtained from the affinity column, and a 65 KDa band, compatible to the known weight of MT-HSP65. Abbreviations: MT-HSP65 (Mycobacterium tuberculosis Heat Shock Protein 65); KDa (kilo Dalton).

FIG. 12A-12C

Anti-CAP1 Antibody Binds Intact THP-1 Cells

Figure 12A:
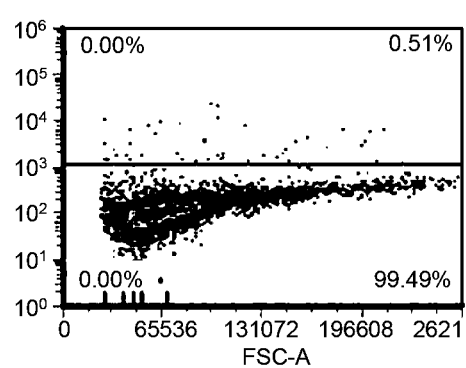
Figure 12B:
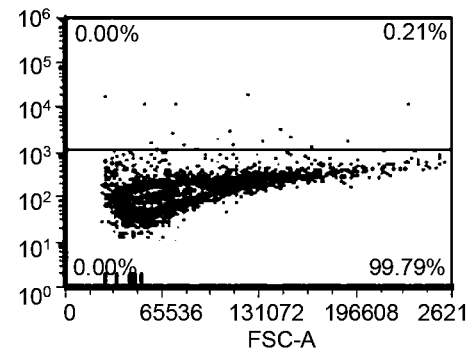
Figure 12C:
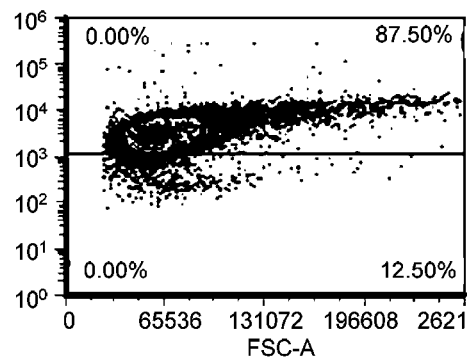

THP-1 cells ($0.5*10^6$/tube) were incubated with 10 μg/ml anti-human CAP1 antibody, followed by staining with goat anti-mouse FITC conjugated IgG, and analyzed by FACS. Unstained cells (FIG. 12A) and FITC stained cells (FIG. 12B) served as negative controls. 87% of the THP-1 cells bound to the anti-CAP1 antibody (FIG. 12C).

FIG. 13A-13C

Anti-CAP1 Antibody does not Bind Intact HeLa Cells

HeLa cells ($10^6$/tube) were incubated with 10 μg/ml anti-human CAP1 antibodies, followed by staining with goat anti-mouse FITC conjugated IgG, and analyzed by FACS. Unstained cells (FIG. 13A) and FITC stained cells (FIG. 13B) served as negative controls. Less than 1.5% of the HeLa cells bound to the anti-CAP1 antibody (FIG. 13C). Abbreviations: Us. (unstained), ce. (cells), α-CAP1 (anti-CAP1 antibody).

FIG. 14A-14C

Anti-CAP1 Antibody Binds Permeablized THP-1 Cells

Figure 14A:
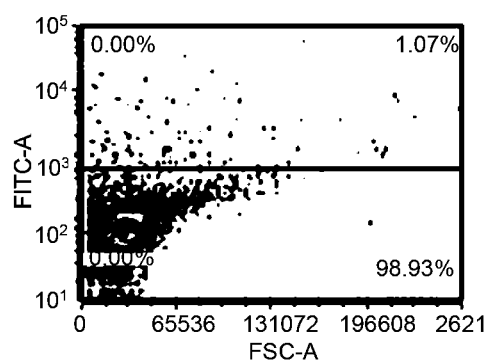
Figure 14B:
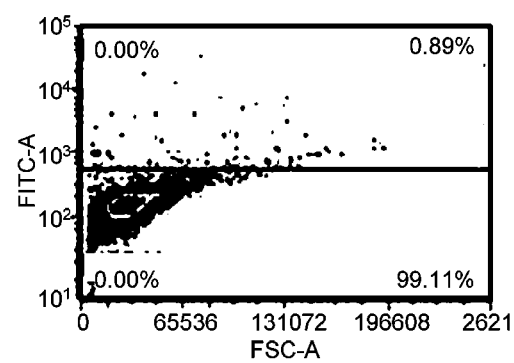
Figure 14C:
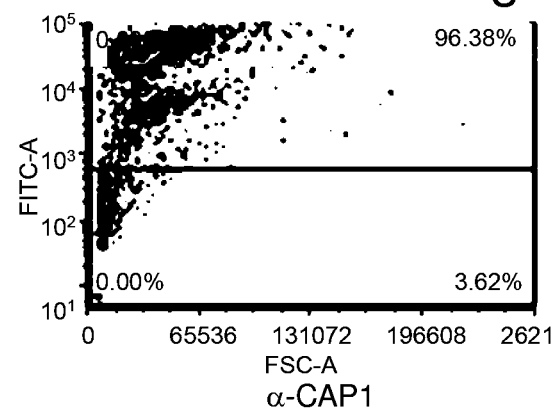

Methanol-permeablized THP-1 cells ($0.5*10^6$/tube) were incubated with 10 μg/ml anti-human CAP1 antibody, followed by staining with goat anti-mouse FITC conjugated IgG, and analyzed by FACS. Unstained cells (FIG. 14A) and FITC stained cells (FIG. 14B) served as negative controls. 96% of the permeabilized THP-1 cells bound to the anti- CAP1 antibody (FIG. 14C). Abbreviations: Us. (unstained), ce. (cells), α-CAP1 (anti-CAP1 antibody).

Figure 15A:
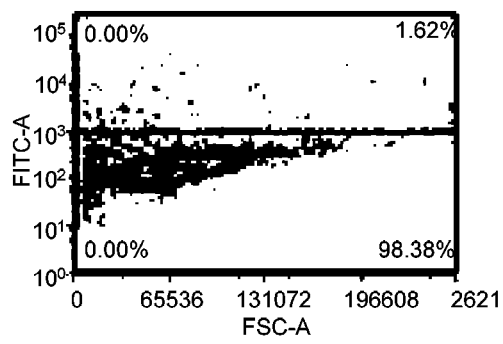
Figure 15B:
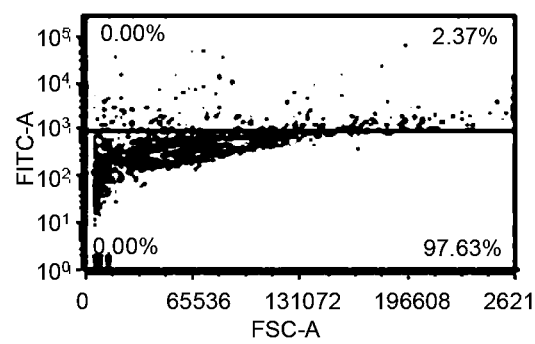
Figure 15C:
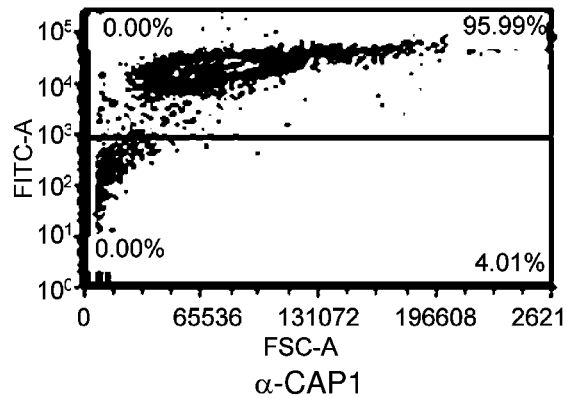

FIG. 15A-15C Anti-CAP1 antibody binds permeabilized HeLa cells

Methanol-permeabilized HeLa cells ($10^6$/tube) were incubated with 10 μg/ml anti-human CAP1 antibodies, followed by staining with goat anti-mouse FITC conjugated IgG, and analyzed by FACS. Unstained cells (FIG. 15A) and FITC stained cells (FIG. 15B) served as negative controls. 96% of the permeabilized HeLa cells bound to the anti-CAP1 antibody (FIG. 15C). Abbreviations: Us. (unstained), ce. (cells), α-CAP1 (anti-CAP1 antibody).

FIG. 16A-16C

Anti-GAPDH Antibody does not Bind Intact THP-1 Cells

Human THP-1 cells were incubated with 1 μg of either mouse anti-CAP1 (FIG. 16B) or mouse anti-GAPDH (FIG. 16C) followed by staining with goat anti-mouse FITC conjugated IgG, and compared with cells stained with secondary antibody only (FIG. 16A) and analyzed by FACS. Anti-GAPDH antibody did not bind the intact THP-1 cells (FIG. 16C), in contrast with anti-CAP1 (FIG. 16B). Abbreviations: Cont. (control); α-CAP1 (anti-CAP1 antibody); α-GAPDH (anti-GAPDH antibody).

FIG. 17A-17C

Anti-GAPDH Antibody Binds Permeabilized THP-1 Cells

Methanol-permeabilized human THP-1 cells were incubated with 1 μg of either anti-CAP1 (FIG. 17B) or anti-GAPDH (FIG. 17C) followed by staining with goat anti-mouse FITC conjugated IgG, and compared with cells stained with secondary antibody only (FIG. 17A) and analyzed by FACS. Both anti-GAPDH and anti-CAP1 bound the permeabilized cells, demonstrating that both antibodies are effective antibodies. Abbreviations: Cont. (control); α-CAP1 (anti-CAP1 antibody); α-GAPDH (anti-GAPDH antibody).

FIG. 18A-18D

Binding of Proximab and Anti-CAP1 Antibodies to CD14+ Mouse Monocyte Cell Line RAW 264.7

Figure 18A:
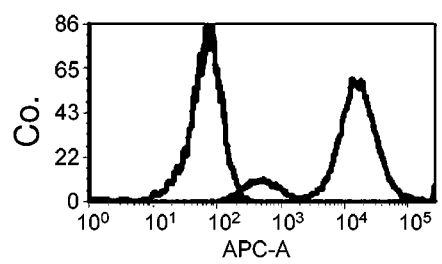
Figure 18B:
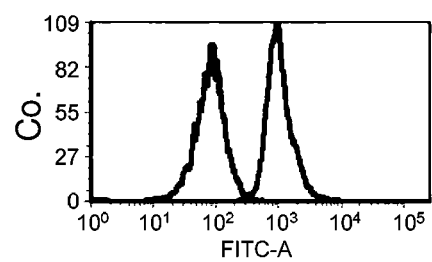
Figure 18C:
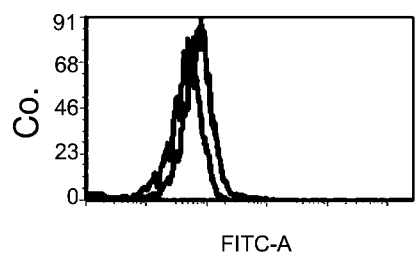

Mouse RAW 264.7 cells were incubated with fluorescently-labeled anti-CD14-APC conjugated) (FIG. 18A), or Proximab-FITC conjugated (FIG. 18B), or anti-GAPDH (FIG. 18C) or anti-CAP1 antibody (FIG. 18D), followed by staining with goat anti-mouse FITC conjugated IgG. Binding profiles of the different antibodies (fluorescent intensity vs. number of cells) were analyzed by FACS and presented herein (Unstained cells—black, stained cells—gray). Abbreviations: Co. (Counts).

FIG. 19A-19D

Proximab and Anti-CAP1 Compete for the Same Ligand

Figure 19A:
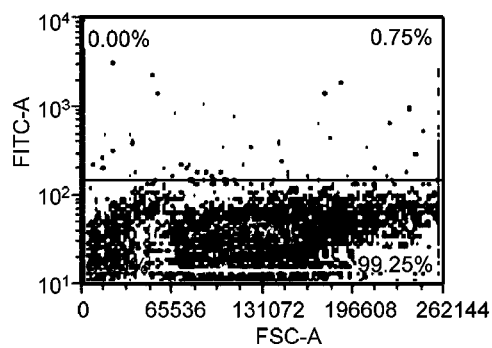
Figure 19B:
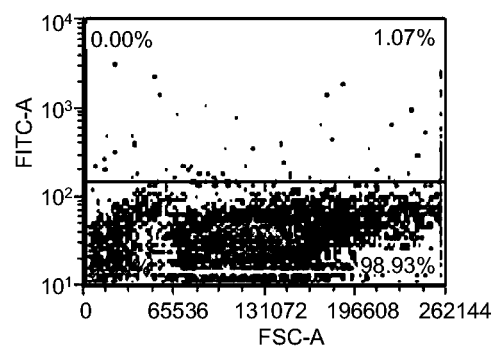
Figure 19C:
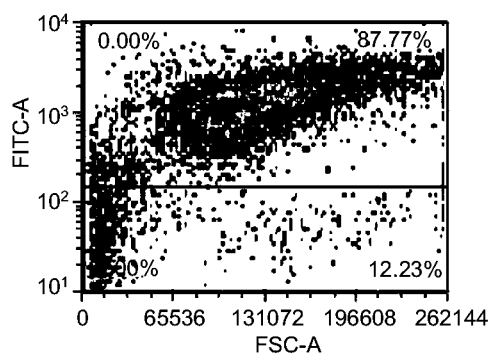

THP-1 cells were pre-incubated with Proximab, followed by staining with anti-human CAP1 (FIG. 19D), and compared to cells incubated only with anti-CAP1 by FACS analysis (FIG. 19C). Unstained cells (FIG. 19A) and FITC stained cells (FIG. 19B) served as negative controls. Pre-incubation with Proximab led to a significant reduction in the population of cells bound to anti-CAP1 antibody (FIG. 19D), as compared to the cells stained with anti-CAP1 alone (FIG. 19C).

FIG. 20

Titration Curve of Proximab Binding to THP-1 Cells

Human THP-1 cells ($0.5*10^6$/tube) were incubated with varying concentrations of Proximab. Following the incubation, the cells were washed and incubated with FITC-conjugated goat anti-human Fc IgG, and analyzed for Proximab binding by flow cytometry. Abbreviations: Ab (antibody); bin. (binding); PROX (anti-peptide-6 humanized Proximab antibody).

FIG. 21

Titration Curve of Anti-CAP1 Binding to THP-1 Cells

Human THP-1 cells ($0.5*10^6$/tube) were incubated with varying concentrations of anti-CAP1. Following the incubation, the cells were washed and incubated with FITC-conjugated goat anti-mouse Fc IgG, and analyzed for anti-CAP1 binding by flow cytometry. Abbreviations: Ab (antibody); bin. (binding), α-CAP1 (anti-CAP1 antibody).

FIG. 22

Specific Knock-Down of CAP1 in THP-1 Cells

Human THP-1 cells were transfected with All Star Negative siRNA or Human CAP1 siRNA (50 pmole/ml each). After 48 hours incubation, cells were harvested and the cells were extracted using 10% SDS protein sample buffer. The cell extracts were resolved on SDS-PAGE and transferred to nitrocellulose membrane by electric power. The nitrocellulose membrane was subjected to Western blotting using mouse anti-CAP1 antibody (50 ng/ml) and re-blotted using anti-alpha-Actin antibody. A specific decrease in CAP1 protein level was observed. Abbreviations: Cont. (All Star Negative siRNA control); α-CAP1 (anti-CAP1 antibody); α-Actin (anti-alpha-Actin antibody).

FIG. 23A-23D

Figures 23A, 23B, 23C, 23D:
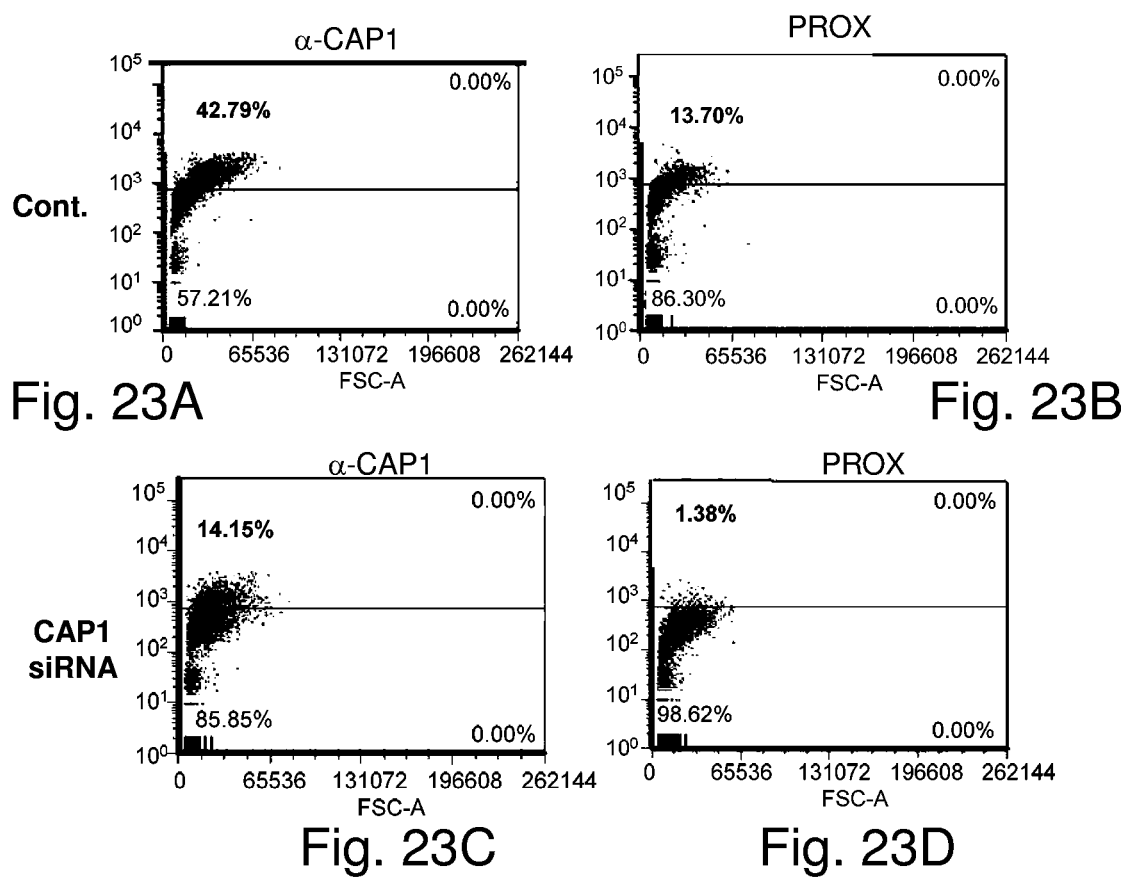

Anti-CAP1 and Proximab Binding to THP-1 Cell Surface is Decreased Upon Treatment with CAP1 siRNA Human THP-1 cells were transfected with All Star Negative siRNA (FIG. 23A, 23B), or Human CAP1 siRNA (FIG. 23C, 23D, 50 pmole/ml each) and incubated with anti-CAP1 antibody (FIG. 23A, 23C, 500 ng/ml) or Proximab (FIG. 23B, 23D, 100 ng/ml). Flow cytometry analysis was carried out using goat anti-mouse and goat anti-human FITC conjugated antibodies. A significant reduction was observed in the binding of both anti-CAP1 (FIG. 23C) and Proximab (FIG. 23D) to the cells following reduction in CAP1 expression via siRNA, in comparison with control cells (FIG. 23A, 23B). Abbreviations: Cont. (All Star Negative siRNA control); PROX (Proximab antibody). α-CAP1 (anti-CAP1 antibody).

FIG. 24A-24B

Figure 24A:
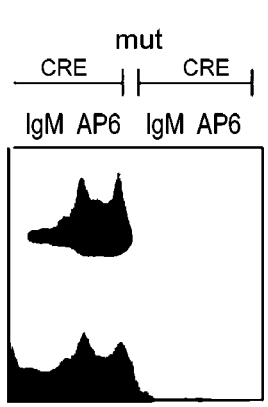
Figure 24B:
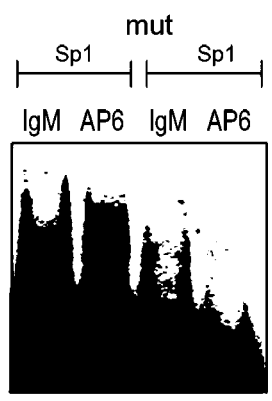

Anti-Peptide-6 Induces Binding of CREB and SP1 Transcription Factors to the IL-10 Promoter Radioactively labeled oligonucleotide probes harboring Sp1 and CRE motifs were incubated with nuclear proteins extracted from PBMC cells incubated with either the B24 anti-peptide-6 antibody or with total Lewis rat IgM antibodies and then analyzed by Electro Mobility Shift Assay (EMSA). Exposure of cells to B24 resulted in significant binding of CREB (FIG. 24A) and Sp1 (FIG. 24B) transcription factors to their corresponding motifs derived from the IL-10 gene promoter, compared to treatment with total Lewis IgM, which showed only negligible protein binding (left-most lane). Mutated CRE and Sp1 abolished B24-induced protein binding to both sites almost completely (right-most lane).

Abbreviations: CRE (cAMP responsive element); mut (mutated); AP6 (B24 anti-peptide-6 antibody).

FIG. 25

Sites of Action of the Protein Kinase A (PKA) Inhibitor KT5720

Figure shows sites of action of the PKA inhibitor KT5720, as indicated with an arrow.

Abbreviations: AC (adenylyl cyclase); Nuc (nucleus); Prot. (protein); In. (inhibitor).

FIG. 26

KT5720 Inhibits IL-10 Induction by Anti-Peptide-6 Antibodies in a Dose-Dependent Manner KT5720 was added in varying concentrations to the PBMCs 15 minutes prior to the incubation with anti-peptide-6 antibody. This resulted in a dose-dependent inhibition of IL-10 secretion.

Abbreviations: DMSO (Dimethyl sulfoxide), UT (untreated).

FIG. 27A-27F

F(ab)$_2$ Fragment of Proximab Binds CD14+ PBMC Cells

Figure 27A:
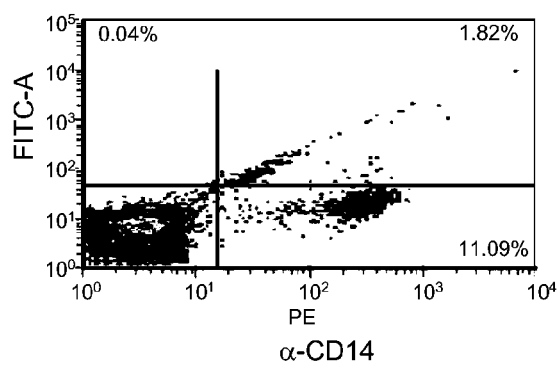
Figure 27B:
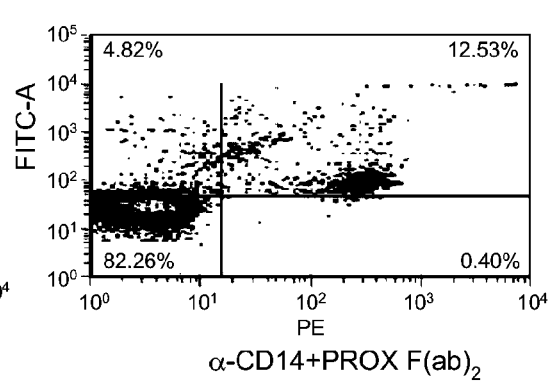
Figure 27C:
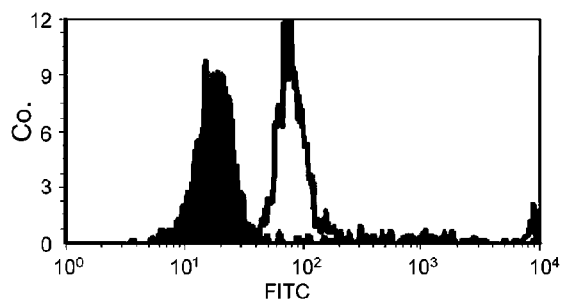

F(ab)$_2$ fragments of Proximab were labeled with FITC using Dylight™ Antibody Labeling Kit (Pierce). Human PBMCs were separated on a Ficoll gradient. The isolated cells were stained with anti-CD14-PE conjugated alone (FIG. 27A) or with together with Proximab F(ab)$_2$-FITC conjugated (FIG. 27B). FIG. 27C depicts the percent of cells out of the CD14+ population that were stained with FITC (Without Proximab F(ab)$_2$—black, With Proximab F(ab)$_2$—gray).

Figure 27D:
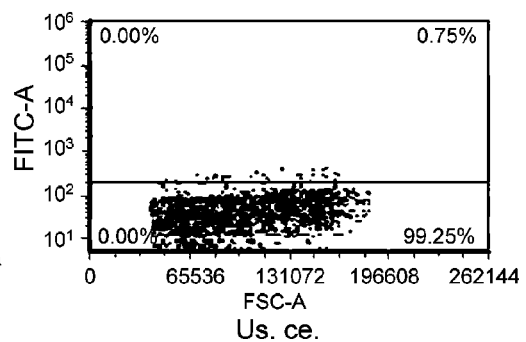
Figure 27E:
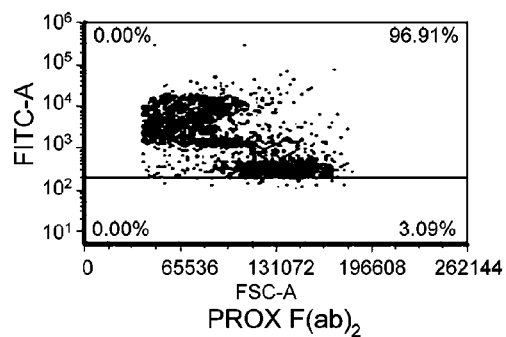
Figure 27F:
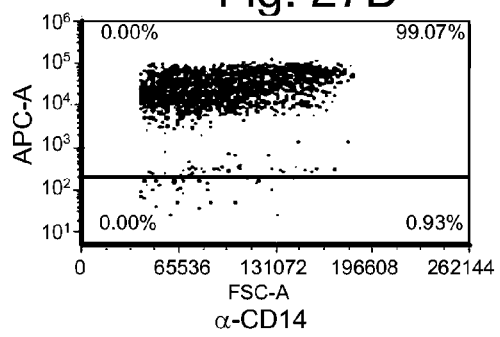

CD14+ PBMC cells were further isolated with anti-human CD14 magnetic beads (BD). The CD14+ isolated cells were either left unstained (FIG. 27D) or stained with anti-CD14-APC conjugated (FIG. 27F) or Proximab F(ab)$_2$-FITC conjugated (FIG. 27E). Proximab F(ab)$_2$ bound a significant percent of the CD14+ population. Abbreviations: Us. (unstained); ce. (cells); co. (counts); α (anti); PROX (Proximab antibody); F(ab)$_2$ (Proximab F(ab)$_2$).

FIG. 28

Proximab, F(ab)$_2$ Fragment of Proximab and Anti-CAP1 Antibody Induce IL-10 Secretion from Human PBMCs Human PBMCs were separated on a Ficoll gradient. The isolated cells were incubated (48 h, 37° C., 5% CO$_2$) in RPMI with either Proximab (200 µg), Proximab F(ab)$_2$ (150 µg) or the anti-CAP1 antibody (8 µg), and IL-10 secretion to the medium was measured by ELISA. Untreated cells served as a control. Abbreviations: PROX (Proximab, anti-peptide-6 humanized antibody); F(ab)$_2$ (F(ab)$_2$ fragment of Proximab); α-CAP1 (anti-CAP1 antibody); UT (untreated).

FIG. 29

Mechanism of Action

Anti-peptide-6 antibodies bind to CAP1 on monocyte cell membranes, thereby inducing a cAMP/PKA-dependent activation of transcription factors, including Sp1 and CRE binding proteins, increasing transcription and secretion of IL-10 and promoting an anti-inflammatory immune response.

Abbreviations: AP6 (anti-peptide-6 antibody); Act. (activation); Sil. (silencing); Rep. (repressors); Path. (pathway); Sec. (secretion).

FIG. 30

*Homo sapiens* CAP1 Amino Acid Sequence

The human CAP1 protein amino acid sequence (GeneBank Accession No. NP_001099000.1, encoded by the human CAP1 gene as shown by GeneBank Accession No. CAG33690.1), also denoted as SEQ ID NO.:6.

DETAILED DESCRIPTION OF THE INVENTION

The present invention demonstrates for the first time a direct interaction between antibodies that specifically recognize an epitope within the HSP65 molecule, the anti-peptide-6 antibodies, and the CAP1 molecule. This interaction leads to induction of the anti-inflammatory cytokine, IL-10. The invention further shows the involvement of cAMP-dependent protein kinase A (PKA), in this anti-peptide-6 antibody pathway. These results clearly demonstrate the role of CAP1 as a key mediator in this immuno-modulatory pathway and therefore as a potential target for immuno-modulation.

The invention further shows activation of IL-10 by anti-CAP1 antibodies and thereby demonstrates the feasibility of using CAP1 and compounds that interact therewith as immunomodulators.

Thus, in the first aspect, the invention relates to a composition for the modulation of the Th1/Th2 balance in a subject in need thereof. According to certain embodiments, the composition of the invention comprises as an active ingredient an immuno-modulatory effective amount of at least one of (a) a compound that interacts with Adenylyl Cyclase-Associated Protein (CAP1); and of (b) CAP1 or any fragment, variant, derivative, homologue and mutant thereof; or any combination thereof. The composition of the invention optionally further comprises a pharmaceutically acceptable carrier, excipient or diluent.

As indicated above, the present invention shows that anti-peptide-6 antibodies bind CAP1 and initiate signaling pathway that leads to increased expression of the anti-inflammatory cytokine IL-10 and thereby to modulation of the Th1/Th2 cell balance.

Therefore, according to some embodiments, the invention's composition comprises as an active ingredient a compound that specifically interacts and binds CAP1, thereby modulating the balance between Th1/Th2 in the subject.

According to certain embodiments, such CAP1-binding compounds may be protein based, nucleic acid based, carbohydrates based, lipid based, natural organic based, synthetically derived organic based, inorganic based, and peptidomimetics based compounds. In one specific embodiment, the compound that binds and interacts specifically with CAP1 may be a protein-based molecule, specifically, an immunoglobulin-like molecule. More specifically, the CAP1-binding compound used by the invention may be an antibody.

It should be further appreciated that according to certain embodiments, the CAP1 binding compounds used by the invention comprise any anti-CAP1 antibody or any antibody that recognizes and binds CAP1, with the proviso that the antibody is not any of the polyclonal, monoclonal, chimeric or humanized anti-peptide-6 antibodies described by the invention or any other antibodies directed to or recognizing peptide-6 (SEQ ID NO. 1).

Still further, according to certain embodiments, the CAP1 binding compound of the invention, that may be an anti-CAP1 antibody, may interact with the CAP1 molecule through a site that is identical to the anti-peptide-6 antibody binding site within the CAP1 molecule, or alternatively, through any different site.

As shown by Example 11, an anti-CAP1 antibody that specifically recognizes and binds CAP1 led to a marked increase in IL-10 expression. Certain embodiments of the invention therefore relate to the composition of the invention wherein the compound serving as the active ingredient may be an isolated and purified anti-CAP1 antibody that specifically recognizes and binds CAP1, thereby modulating the balance between Th1/Th2 towards the Th2 anti-inflammatory response.

According to certain embodiments, a Th2 anti-inflammatory response involves an increase in the expression of an anti-inflammatory cytokine. Such anti-inflammatory cytokine may be any one of IL-10, IL-4, IL-6, IL-11, IL-13 and IL-1 receptor antagonist. According to certain embodiments, the Th2 anti-inflammatory response involves an increase in IL-10 expression. More specifically, such increase may be an increase of between about 10% to 100%, 10% to 90%, 10% to 80%, 10% to 70%, 10% to 60% or 10% to 50% of the expression of such cytokines. Particularly, an increase of 10%, 20%, 30%, 40%, 50%, 60%, 70%, 80%, 90%, 95% or 100% of the expression as compared with a suitable control, specifically, untreated subjects or cells.

According to the above and other embodiments, the invention provides antibodies that specifically recognize and bind CAP1 for use in the composition of the invention. It should be therefore noted that the term "binding specificity", "specifically binds to CAP1", "specifically immuno-reactive with CAP1", "specifically directed against CAP1" or "specifically recognizes", when referring to an epitope within the CAP1 molecule, refers to a binding reaction which is determinative of the presence of the epitope in a heterogeneous population of proteins and other biologics. Thus, under designated immunoassay conditions, the specified antibodies bind to a particular epitope at least two times the background and more typically more than 10 to 100 times background.

The term "epitope" is meant to refer to that portion of any molecule, specifically of CAP1, capable of being recognized and bound by an antibody. Epitopes or "antigenic determinants" usually consist of chemically active surface groupings of molecules such as amino acids or sugar side chains and have specific three dimensional structural characteristics as well as specific charge characteristics.

As indicated above, in certain embodiments, the invention provides isolated and purified anti-CAP1 antibodies. As used herein, "isolated" or "substantially purified", in the context of an antibody or nucleic acid molecule encoding an antibody, means the antibody or nucleic acid has been removed from its natural milieu or has been altered from its natural state. As such "isolated" does not necessarily reflect the extent to which the antibody or nucleic acid molecule has been purified. However, it will be understood that an antibody or nucleic acid molecule that has been purified to some degree is "isolated". If the antibody or nucleic acid molecule does not exist in a natural milieu, i.e. it does not exist in nature, the molecule is "isolated" regardless of where it is present.

It should be noted that the anti CAP1 antibodies used by the composition of the invention may be any one of polyclonal and monoclonal antibodies. Generation of polyclonal antibodies against proteins is described in, for example, Chapter 2 of Current Protocols in Immunology, Wiley and Sons Inc.

Monoclonal antibodies may be prepared from B cells taken from the spleen or lymph nodes of immunized animals, in particular rats or mice, by fusion with immortalized B cells under conditions which favor the growth of hybrid cells. The technique of generating monoclonal antibodies is described in many articles and textbooks, such as the above-noted Chapter 2 of Current Protocols in Immunology.

As used herein, the term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Antibodies may exist as intact immunoglobulins, or as modifications in a variety of forms including, for example, an Fv fragment containing only the light and heavy chain variable regions, a F(ab) or F(ab)'2 fragment containing the variable regions and parts of the constant regions, a single-chain antibody, and the like. The antibody may be of animal or human origin or may be chimeric or humanized. As used herein the term "antibody" includes these various forms.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

As indicated herein above, according to certain embodiments, the invention provides the use of anti-CAP1 antibody and any antigen binding fragment thereof as an active ingredient in the immuno-modulatory composition. The term "an antigen-binding fragment" refers to any portion of an antibody that retains binding to CAP1. Examples of antibody functional fragments include, but are not limited to, complete antibody molecules, antibody fragments, such as Fv, single chain Fv (scFv), complementarity determining regions (CDRs), $V_L$ (light chain variable region), $V_H$ (heavy chain variable region), Fab, F(ab)$_2$' and any combination of those or any other functional portion of an immunoglobulin peptide capable of binding to target antigen. As appreciated by one of skill in the art, various antibody fragments can be obtained by a variety of methods, for example, digestion of an intact antibody with an enzyme, such as pepsin or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries. The term antibody also includes bivalent molecules, diabodies, triabodies, and tetrabodies.

References to "$V_H$" or a "VH" refer to the variable region of an immunoglobulin heavy chain, including an Fv, scFv, a disulfilde-stabilized Fv (dsFv) or Fab. References to "$V_L$" or a "VL" refer to the variable region of an immunoglobulin light chain, including of an Fv, scFv, dsFv or Fab.

More specifically, the phrase "single chain Fv" or "scFv" refers to an antibody in which the variable domains of the heavy chain and of the light chain of a traditional two chain antibody have been joined to form one chain. Typically, a linker peptide is inserted between the two chains to allow for the stabilization of the variable domains without interfering with the proper folding and creation of an active binding site. A single chain anti CAP1 antibody used by the invention, may bind as a monomer. Other exemplary single chain antibodies may form diabodies, triabodies, and tetrabodies.

It should be appreciated that the anti-CAP1 antibodies used by the compositions and methods of the invention may be humanized antibodies. As used herein, the term "humanized" refers to forms of non-human (e.g. murine) antibodies which are specific chimeric immunoglobulins, immunoglobulin chains, or fragments thereof (such as Fv, Fab, Fab', F (ab')2 or other antigen-binding subsequences of antibodies) and which contain minimal sequence derived from non-human immunoglobulin. For the most part, humanized antibodies are human immunoglobulins in which residues from a hypervariable region of the recipient are replaced by residues from a hypervariable region of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody or the donor antibody. These modifications are made to further refine and optimize antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

As indicated herein before and shown by the following Examples, anti-CAP1 antibody led to a marked increase in the expression of the anti-inflammatory cytokine, IL-10. According to certain embodiments, a Th2 anti-inflammatory response involves an increase in the expression of an anti-inflammatory cytokine. Such anti-inflammatory cytokine may be any one of IL-10, IL-4, IL-6, IL-11, IL-13 and IL-1 receptor antagonist. According to certain embodiments, the Th2 anti-inflammatory response involves an increase in IL-10 expression. More specifically, such increase may be an increase of between about 10% to 100%, 10% to 90%, 10% to 80%, 10% to 70%, 10% to 60% or 10% to 50% of the expression of such cytokines. Particularly, an increase of 10%, 20%, 30%, 40%, 50%, 60%, 70%, 80%, 90%, 95% or 100% of the expression as compared with a suitable control, specifically, untreated subjects or cells.

Demonstration of CAP1 as a key target for immuno-modulation by the present invention provides the use of an isolated and purified CAP1 protein or any fragment thereof as an immuno-modulator. Therefore, according to other embodiments, the invention provides compositions comprising as an active ingredient CAP1 or any fragment, variant, derivative, homologue and mutant thereof, thereby modulating the balance between Th1/Th2 in the subject.

The term "isolated" or "substantially purified", when applied to a nucleic acid or protein, such as the CAP1 molecule, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified.

It should be noted that the isolated and purified CAP1 molecule or any fragment thereof used by the composition of the invention, may be provided as any one of a purified recombinant protein, and a cell lysate or membrane preparation of a transformed host cell expressing the CAP1 molecule. The terms fragments and functional fragments used herein mean the CAP1 molecule or any fragment, variant homolog or derivative thereof, with any insertions, deletions, substitutions and modifications, that is capable of inducing specific modulation of the Th1/Th2 cell balance (hereafter referred to as "fragment/s"), as reflected by activation of Th2 anti-inflammatory cytokines, for example, IL-10, or alternatively, Th1 pro-inflammatory cytokines. It should be appreciated that according to certain embodiments used herein in the specification and in the claim section below, the CAP1 protein refer to a protein having the amino acid sequence of human CAP1, or any fragment, variant homolog or derivative thereof. An example for a human CAP1 protein is a protein comprising the amino acid sequence as denoted by GeneBank Accession No. NP_001099000.1, shown by FIG. 30 and also denoted as SEQ ID NO.:6, encoded by the human CAP1 gene as shown by GenBank Accession No. CAG33690.1.

With respect to amino acid sequences, for example, the amino acid sequence of the CAP1 protein, specifically, the human CAP1, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

The term "derivative" is used to define amino acid sequence variants, and covalent modifications of a polypeptide made use of in the present invention. e.g. of a specified sequence. The functional derivatives of a CAP1 polypeptide utilized according to the present invention, e.g. of a specified sequence of CAP1, preferably have at least about 65%, more preferably at least about 75%, even more preferably at least about 85%, most preferably at least about 95% overall sequence homology with the amino acid sequence of the CAP1 polypeptide as structurally defined above, e.g. of a specified sequence, more specifically, an amino acid sequence of CAP1 as denoted by SEQ ID NO. 6.

"Homology" with respect to a native CAP1 polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- nor C-terminal extensions nor insertions or deletions shall be construed as reducing identity or homology. Methods and computer programs for the alignment are well known. It should be appreciated that by the terms "insertions" or "deletions", as used herein it is meant any addition or deletion, respectively, of amino acid residues to the CAP1 molecule used by the invention, of between 1 to 50 amino acid residues, between 20 to 1 amino acid residues, and specifically, between 1 to 10 amino acid residues. More particularly, insertions or deletions may be of any one of 1, 2, 3, 4, 5, 6, 7, 8, 9, or 10 amino acids.

The terms "identical", "substantial identity", "substantial homology" or percent "identity", in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region.

"Amino acid(s)" refer to all naturally occurring L-amino acids, e.g. and including D-amino acids. The amino acids are identified by either the well known single-letter or three-letter designations.

The invention also provides a therapeutic composition for the modulation of the Th1/Th2 balance in a subject in need thereof, comprising as an active ingredient an immuno-modulatory effective amount of at least one of a compound that interacts with Adenylyl Cyclase-Associated Protein (CAP1) and of CAP1 or any fragment, variant, derivative, homologue and mutant thereof, or any combination thereof, the composition optionally further comprises a pharmaceutically acceptable carrier, excipient or diluent, for treating, preventing, ameliorating or delaying the onset of an immune-related disorder.

Thus, according to one embodiment, the invention provides a therapeutic composition for the treatment of an immune related disorder. The composition of the invention comprises as an active ingredient a compound that specifically interacts and binds CAP1. A non-limiting example for such compound is an anti-CAP1 antibody.

In yet another embodiment, the pharmaceutical composition of the invention comprises CAP1 and any fragments, derivatives and variants thereof as an active ingredient.

Therefore, use of the composition of the invention for the treatment of an immune-related disorder in a subject in need thereof, is further provided.

As used herein, the term "disorder" or "condition" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

The term "immune-related disorders" relates to an imbalance in the Th1-Th2 response.

Compounds which interact with CAP1 and modulate the expression of an anti-inflammatory cytokine may therefore increase the expression of such cytokine, IL-10 for example. Such compounds may be useful in conditions where modulation of the Th1/Th2 balance towards an anti-inflammatory reaction is desired. For example, in the treatment of immune-related disorders such as an autoimmune disease, (for example, Arthritis, multiple sclerosis (MS), Type-1 diabetes, lupus, Graves disease and thyroiditis, IBD), graft rejection pathology and graft versus host disease, and disorders induced by supper antigens, such as toxic shock, septic shock and severe sepsis.

According to certain embodiments, the CAP-1 binding compound used by the invention, specifically, the anti-CAP1 antibody, by enhancing Th2 an anti-inflammatory response, may be useful for treatment of or amelioration of inflammatory symptoms in any disease, condition or disorder where immune and/or inflammation suppression is beneficial such as, but not limited to, treatment of or amelioration of autoimmune and inflammatory symptoms in the joints, musculoskeletal and connective tissue disorders, or of autoimmune and inflammatory symptoms associated with hypersensitivity, allergic reactions, asthma, atherosclerosis, neuro-inflammatory and neurodegenerative diseases, inflammatory bowel diseases, otitis and other otorhinolaryngological diseases, dermatitis and other skin diseases, posterior and anterior uveitis, conjunctivitis, optic neuritis, scleritis, and other immune and/or inflammatory ophthalmic diseases.

More particularly, in general, the composition as well as the methods of the present invention using an immuno-modulatory compound that binds CAP1, may be used in the treatment of any autoimmune disease such as for example, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pemphigoid, dermatitis herpetiformis, insulin dependent diabetes, inflammatory bowel disease, ulcerative colitis and Crohn's disease.

Alternatively, the immuno-modulating compound that binds CAP1 may lead to decrease of anti-inflammatory cytokines expression. This may shift the Th1/Th2 balance towards the Th1 pro-inflammatory reaction. Compounds modulating the immune-reaction towards a pro-inflammatory reaction may be useful for treating immune-related disorders such as proliferative pathologic conditions. Thus, the invention further provides compositions and methods for treating any immune-related disorder.

More specifically, such proliferative condition may be a malignant disorder. According to a specific embodiment, the malignant proliferative disorder may be any one of solid and non-solid tumor selected from the group consisting of carcinoma, sarcoma, melanoma, leukemia and lymphoma. More particularly, the malignant disorder may be melanoma, hepaotcellular carcinoma, colon cancer, myeloma, acute or chronic leukemia.

As used herein to describe the present invention, the terms "malignant proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the composition as well as the methods of the present invention may be used in the treatment of non-solid and solid tumors, for example, carcinoma, melanoma, leukemia, and lymphoma.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

It should be noted that the pharmaceutical composition of the invention may comprise the active compound in free form and be administered directly to the subject to be treated. Alternatively, depending on the size of the active molecule, it may be desirable to conjugate it to a carrier prior to administration. Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intraperitoneal (IP), intravenous (IV) and intradermal) administration.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

The pharmaceutical compositions of the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

The nature, availability and sources, and the administration of all such compounds including the effective amounts necessary to produce desirable effects in a subject are well known in the art and need not be further described herein. The preparation of pharmaceutical compositions is well known to the skilled man of the art and has been described in many articles and textbooks, see e.g., Remington's Pharmaceutical Sciences, Gennaro A. R. ed., Mack Publishing Co., Easton, Pa., 1990, and especially pp. 1521-1712 therein.

Pharmaceutical compositions comprising the compound that binds CAP1, for example, the anti-CAP1 antibodies or the CAP1 protein or any fragments thereof used by the present invention are useful for parenteral administration, i.e., intraperitoneally (i.p.), subcutaneously (s.c.), intramuscularly (i.m.) and intravenously (i.v.). The compositions for parenteral administration commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate. The concentration of the CAP1 binding compound, for example the anti-CAP1 antibodies in these formulations can vary widely, i.e., from less than about 0.01%, usually at least about 0.1% to as much as 5% by weight and will be selected primarily based on fluid volumes, and viscosities in accordance with the particular mode of administration selected.

More specifically, injectable compositions that include the CAP1-binding compound, for example, the anti-CAP1 antibodies used by the invention, or the CAP1 molecule or any fragments thereof, may be prepared in water, saline, isotonic saline, phosphate-buffered saline, citrate-buffered saline, and the like and may optionally mixed with a nontoxic surfactant. Under ordinary conditions of storage and use, these preparations may contain a preservative to prevent the growth of microorganisms. Pharmaceutical dosage forms suitable for injection or infusion include sterile, aqueous solutions or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. Isotonic agents such as sugars, buffers, or sodium chloride may be included. Prolonged absorption of the injectable compositions can be brought about by the inclusion in the composition of agents delaying absorption, for example, aluminum monosterate hydrogels and gelatin. Solubility enhancers may be added.

Sterile injectable compositions may be prepared by incorporating CAP1-binding compound, for example, the anti-CAP1 antibodies, or alternatively, the CAP1 molecule and any fragments thereof, in the desired amount in the appropriate solvent with various other ingredients, e.g. as enumerated above, and followed by sterilization, as desired, by, for example filter sterilization. In the case of sterile powders for the preparation of sterile injectable solutions, methods of preparation include vacuum drying and freeze-drying techniques, which yield a powder of the active ingredient plus any additional desired ingredient present in a previously sterile-filtered solution. Any suitable sterilization process may be employees, such as filter sterilization, e.g. 0.22 micron filter or nanofiltration, gamma or electron beam sterilization.

In various embodiments, the final solution is adjusted to have a pH between about 4 and about 9, between about 5 and about 7, between about 5.5 and about 6.5, or about 6. The pH of the composition may be adjusted with a pharmacologically acceptable acid, base or buffer.

Still further, the compositions of the invention may be presented in unit dose forms containing a predetermined amount of each active ingredient per dose. Such a unit may be adapted to provide 0.001-100 mg/Kg of body weight of the CAP1-binding compound, for example, the anti-CAP1 antibodies used by the invention. Specifically, either 0.01-50 mg/Kg, 0.1-10 mg/Kg, 0.5-10 mg/Kg, 1-10 mg/Kg, 5-15 mg/Kg, 10-30 mg/Kg, 25-50 mg/Kg 40-80 mg/Kg or 60-100 mg/Kg. Such doses can be provided in a single dose or as a number of discrete doses. The ultimate dose will of course depend on the condition being treated, the route of administration and the age, weight and condition of the patient and will be at the doctor's discretion.

As indicated above, in addition to the parenteral route, the compositions of the invention may be adapted for administration by any other appropriate route, for example by the oral (including buccal or sublingual), rectal, nasal, topical (including buccal, sublingual or transdermal) or vaginal route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets, powders or granules, solutions or suspensions in aqueous or non-aqueous liquids, edible foams or whips, or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either paraffin or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurized aerosols, nebulizers or insufflators.

Pharmaceutical formulations adapted for vaginal administration may be presented as pessaries, tampons, creams, gels, pastes, foams or spray formulations.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavoring agents.

It should be further noted that the compositions of the invention, can be administered for prophylactic and/or therapeutic treatments. In therapeutic application, compositions are administered to a patient already affected by an immune-related disorder (e.g., arthritis, IBD and diabetes) in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.001 to about 100 mg/Kg of CAP1 binding protein, specifically, an anti-CAP1 antibody, with dosages of from 0.01 to 50 mg and 0.1 to 10 mg per Kg of body weight being more commonly used. Single or multiple administrations on a daily, weekly or monthly schedule can be carried out with dose levels and pattern being selected by the treating physician.

In prophylactic applications, compositions containing the anti-CAP1 antibodies are administered to a patient who is at risk of developing the disease state to enhance the patient's resistance. Such an amount is defined to be a "prophylactically effective dose". In this use, the precise amounts again depend upon the patient's state of health and general level of immunity, but generally range from 0.001 to 100 mg per dose, especially 0.01-10 mg per dose, 0.1-10 mg per dose or 1 to 10 mg per dose or alternatively, per Kg of body weight.

Single or multiple administrations of the compositions are administered depending on the dosage and frequency as required and tolerated by the patient. In any event, the composition should provide a sufficient quantity of the CAP1 binding compound, specifically, the anti-CAP1 antibodies used by this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the compositions of the present invention can be made as implants, oily injections, or as particulate systems.

Particulate systems include microspheres, microparticles, microcapsules, nanocapsules, nanospheres, and nanoparticles. Microcapsules contain the therapeutic compositions as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly.

According to a second aspect, the invention provides a method for treating, preventing, ameliorating or delaying the onset of an immune-related disorder in a subject in need thereof. The method of the invention involves the step of administering to the subject a therapeutically effective amount of at least one of (a) a compound that interacts with Adenylyl Cyclase-Associated Protein (CAP1) and/or of (b) CAP1, or any fragment, variant, derivative, homologue and mutant thereof, or any combination thereof or any composition comprising the same.

In one specific embodiment, the method of the invention comprises the step of administering to the subject a therapeutically effective amount of a compound that specifically interacts and binds CAP1 or of any composition comprising the same, thereby modulating the balance between Th1/Th2 in the treated subject.

According to certain embodiments, such CAP1-binding compounds may be protein based, nucleic acid based, carbohydrates based, lipid based, natural organic based, synthetically derived organic based, inorganic based, and peptidomimetics based compounds. In one specific embodiment, the compound that binds and interacts specifically with CAP1 may be a protein-based molecule, specifically, an immunoglobulin-like molecule. More specifically, the CAP1-binding compound used by the methods and compositions of the invention may be an antibody. Specific examples for such antibodies are the anti-CAP1 antibodies and the anti-peptide-6 antibodies that specifically interact either directly or indirectly with CAP1, leading to enhancement in IL-10 expression. Example 11 herein below discloses the use of anti-CAP1 antibodies for induction of IL-10 expression.

It should be further appreciated that according to certain embodiments, the CAP1 binding compounds used by the invention comprise any anti-CAP1 antibody or any antibody that recognizes and binds CAP1, with the proviso that the antibody is not any of the polyclonal, monoclonal, chimeric or humanized anti-peptide-6 antibodies described by the invention or in previous publications and applications of the present inventors, or any other antibodies directed to, or recognizing peptide-6 (SEQ ID NO. 1).

More specifically, is some embodiments the method of the invention comprises the step of administering to the subject a compound that is an anti-CAP1-antibody that specifically recognizes and binds CAP1, thereby modulating the balance between Th1/Th2 towards the Th2 anti-inflammatory response in the subject.

It should be noted that the anti CAP1 antibodies used by the method of the invention may be any one of polyclonal, monoclonal, chimeric or humanized antibodies. Generation of polyclonal antibodies against proteins is described in, for example, Chapter 2 of Current Protocols in Immunology, Wiley and Sons Inc.

Monoclonal antibodies may be prepared from B cells taken from the spleen or lymph nodes of immunized animals, in particular rats or mice, by fusion with immortalized B cells under conditions which favor the growth of hybrid cells. The technique of generating monoclonal antibodies is described in many articles and textbooks, such as the above-noted Chapter 2 of Current Protocols in Immunology.

The term "antibody" is meant to include intact molecules as well as fragments thereof, such as, for example, Fab and $F(ab')_2$, which are capable of binding antigen [Wahl et al., J. Nucl. Med. 24:316-325 (1983)].

It will be appreciated that Fab and $F(ab')_2$ and other fragments of the antibodies useful in the present invention may be used, according to the methods disclosed herein for intact antibody molecules. Such fragments are typically produced by proteolytic cleavage, using enzymes such as papain (to produce Fab fragments) or pepsin (to produce $F(ab')_2$ fragments).

In yet other alternative embodiments, the method of the invention comprises the step of administering to the subject a therapeutically effective amount of CAP1 or any fragment, variant, derivative, homologue and mutant thereof or any composition comprising the same, thereby modulating the balance between Th1/Th2 in the subject.

It should be appreciated that CAP1 as used herein refer to human CAP1 protein comprising the amino acid sequence as denoted by GenBank Accession No. NP_001099000.1 presented by FIG. 30 and also denoted as SEQ ID NO.:6, encoded by the human CAP1 gene as denoted by GenBank Accession No. CAG33690.1.

By "patient" or "subject in need" treated by the compositions and methods of the invention it is meant any mammal who may be affected by the above-mentioned conditions, and to whom the treatment methods herein described is desired, including human, bovine, equine, canine, murine and feline subjects. Preferably said patient is a human. Administering of the compositions of the invention, to the patient includes both self-administration and administration to the patient by another person.

According to another specific embodiment, the active ingredients used by the invention or composition comprising the same, may be administered via any mode of administration. For example, oral, intravenous, intramuscular, subcutaneous, intraperitoneal, parenteral, transdermal, intravaginal, intranasal, mucosal, sublingual, topical, rectal or subcutaneous administration, or any combination thereof.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. According to certain embodiments, the therapeutic effective amount may range between about 0.001 to 100 mg/Kg. Specific embodiment comprises 0.001-100 mg/Kg of body weight of the CAP1-binding compound, for example, the anti-CAP1 antibodies used by the invention. Specifically, either 0.01-10 mg/Kg, 0.1-10 mg/Kg, 0.5-10 mg/Kg, 1-10 mg/Kg, 5-15 mg/Kg, 10-30 mg/Kg, 25-50 mg/Kg 40-80 mg/Kg or 60-100 mg/Kg.

Still further, in certain embodiments a therapeutically effective amount of any of the CAP1 binding compounds or CAP1 molecules administered daily by the method of the invention may range from about 0.001 mg/kg to about 10 mg/kg of body weight, specifically, between about 0.010 to 8 or 0.020 to 6, 0.030 to 5 mg/kg. According to a specific embodiment, the effective amount may be any one of 0.01, 0.1, 0.5, 1, 5, 10, 20, 30, 40, 50, 60, 70, 80, 90, 100, 150, 200, 250, 300, 350, 400, 450 and 500 mg, optionally, per day. Specifically, the effective amount may be about 0.01 to 1000 mg per day, 10 to 500 mg per day, more specifically, any one of 0.01, 0.1, 1, 10, 50, 100, 150, 200, 250, 300, 350, 400, 450 and 500 mg per day. It should be appreciated that such effective amount is specific for mice. Still further, it should be recognized that generally "human doses" may be calculated by dividing doses (mg/kg) in mice by about 12 to derive respective Human Equivalent Doses (HED) (mg/kg), and further divided by 10 (Safety Factor in extrapolating from mice to human), in accordance with the Guidance for Industry, Estimating the Maximum Safe Starting Dose in Initial Clinical Trials for Therapeutics in Adult Healthy Volunteers. This effective amount of the CAP-1 binding compound or alternatively, the CAP1 molecule is preferably comprised within a dosage unit form. Additionally, the administration of the compositions according to the invention may be periodically, for example, the periodic administration may be effective twice daily, three times daily or at least one daily for at least about three days to three months. The advantages of lower doses are evident to those of skill in the art. These include, inter alia, a lower risk of side effects, especially in long-term use, and a lower risk of the patients becoming desensitized to the treatment.

According to another embodiment, the dosage unit form used by the method of the invention may be either for a single or for repeated administration. According to another embodiment, administration of said dosage unit form is repeated every one to five, ten or twenty four hours, for a therapeutically sufficient period of time. According to an alternative embodiment, the dosage unit form may be a sustained-released dosage unit form which provides continues pH independent drug release for a considerable period of time after administration.

It should be noted that while treatment of other adverse indications may be effected using doses of the CAP1-binding compound used by the invention in the range of from about 0.001 mg per day to about 1000 mg per day, about 0.01 mg per day to about 500 mg per day, 0.1 mg per day to about 500 mg per day, about 1 mg per day to about 500 mg per day or about 10 mg per day to about 500 mg per day and/or may be effected following at least between one days to about treatment for life. In another embodiment, treatment using the CAP-1 binding compounds of the invention may be effected following at least 1, 2, 3, 4, 5, 6, 7, 8, 9, 10, 14, 30, 60, 90 days of treatment, and proceeding on to treatment for life.

It should be noted that the treatment of different conditions may indicate the use of different doses or different time periods; these will be evident to the skilled medical practitioner.

As indicated above, the invention provides methods and pharmaceutical compositions specifically suitable for treating an immune-related disorder, for example, an autoimmune or inflammatory disorder.

The following Examples clearly demonstrate the applicability of the compositions and methods of the invention for treating established inflammatory arthritis. More specifically, Lewis rats treated for AA induction and concomitantly with the anti-peptide-6 humanized antibody of the invention that was shown to interact with CAP1, showed a significant reduction in arthritis.

Other compounds interacting with CAP1, for example, an anti-CAP1 antibody, showed clear induction of anti-inflammatory response, as demonstrated by enhancement of IL-10 expression. These compounds may be therefore applicable as immunomodulators for treating immune-related disorders.

It should be noted that, as indicated by Berent, J. et al., [Berent, J. et al., Springer Semin. Immunopathol. 25: 7-63 (2003)], adjuvant arthritis (AA) is a well established animal model for rheumatoid arthritis (RA), juvenile idiopathic arthritis (JIA) and septic arthritis.

There are different forms of arthritis that may be generally grouped into two main categories, inflammatory arthritis, and degenerative arthritis, each has a different cause. Therefore, according to one specific embodiment, the methods and pharmaceutical compositions of the invention may be specifically intended for the treatment and/or amelioration of an inflammatory disorder, for example, an inflammatory arthritis.

Inflammatory arthritis is characterized by synovitis, bone erosions, osteopenia, soft-tissue swelling, and uniform joint space narrowing. More specifically, the hallmarks of joint inflammation are synovitis and erosion of bone. The latter will initially appear as a focal discontinuity of the thin, white, subchondral bone plate. Normally, this subchondral bone plate can be seen even in cases of severe osteopenia, whereas its discontinuity indicates erosion. Although it is true that periarticular osteopenia and focal subchondral osteopenia can appear prior to true bone erosion, it is the presence of bone erosion that indicates definite joint inflammation. As the bone erosion enlarges, osseous destruction extends into the trabeculae within the medullary space. One important feature of inflammatory arthritis relates to the concept of marginal bone erosion. This term is given to bone erosion that is located at the margins of an inflamed synovial joint. This specific location represents that portion of the joint that is intraarticular but not covered by hyaline cartilage. Therefore, early joint inflammation will produce marginal erosions prior to erosions of the subchondral bone plate beneath the articular surface. When looking for bone erosions, multiple views of a joint are essential to profile the various bone surfaces. A second important characteristic of an inflammatory joint process is uniform joint space narrowing. This occurs because destruction of the articular cartilage is uniform throughout the intraarticular space. A third finding of inflammatory joint disease is soft-tissue swelling.

It should be appreciated that inflammatory arthritis may be further divided into several subgroups, and therefore, the compositions, as well as the methods of the invention described herein, may be applicable for treating every inflammatory arthritis condition of the different subgroups.

More specifically, involvement of a single joint is indicative of a Septic arthritis. The cause of septic arthritis is usually related to hematogenous seeding owing to staphylococcal or streptococcal microorganisms. The radiographic features of a septic joint encompass those of any inflammatory arthritis, namely, periarticular osteopenia, uniform joint space narrowing, soft-tissue swelling, and bone erosions. Not all findings may be present simultaneously, and, acutely, bone erosions may not be evident. Thus, according to one embodiment, the compositions and methods of the invention may be used for the treatment and/or amelioration of septic arthritis.

A systemic arthritis, in contrast, is characterized by involvement multiple joints, and includes two main categories, rheumatoid arthritis and seronegative spondyloarthropathy.

According to one embodiment, the compositions as well as the methods of the invention may be used for the treatment and/or amelioration of rheumatoid arthritis. Rheumatoid arthritis (RA) is a chronic, systemic autoimmune disorder that most commonly causes inflammation and tissue damage in joints (arthritis) and tendon sheaths, together with anemia. It can also produce diffuse inflammation in the lungs, pericardium, pleura, and the sclera of the eye, and also nodular lesions, most common in subcutaneous tissue under the skin. It can be a disabling and painful condition, which can lead to substantial loss of functioning and mobility. Serologic markers such as rheumatoid factor and antibodies to cyclic citrullinated peptide are important indicators of rheumatoid arthritis. The radiographic features of rheumatoid arthritis are those of joint inflammation and include particular osteopenia, uniform joint space loss, bone erosions, and soft-tissue swelling. Because of the chronic nature of the inflammation, additional findings such as joint subluxation and subchondral cysts may also be evident.

The seronegative spondyloarthropathy category includes psoriatic arthritis, reactive arthritis, and ankylosing spondylitis, and is characterized by signs of inflammation, multiple joint involvement, and distal involvement in the hands and feet with added features of bone proliferation. Thus, according to one embodiment, the compositions and methods of the invention may be used for the treatment and/or amelioration of any condition of the seronegative spondyloarthropathy category.

More specifically, according to one embodiment, the compositions and methods of the invention may be used for the treatment and/or amelioration of psoriatic arthritis. Psoriatic arthritis is a chronic disease characterized by inflammation of the skin (psoriasis) and joints (arthritis). Nearly 306,000 people in the USA suffer from psoriatic arthritis and additional 308,000 people are believed to suffer from the disease in the five leading markets in Europe. Psoriasis and arthritis often appear separately. In fact, the skin disease precedes the arthritis in nearly 80% of patients. The arthritis may precede the psoriasis in up to 15% of patients.

Psoriasis, one of the characteristics of psoriatic arthritis, is a common skin condition that features patchy, raised, red areas of skin inflammation with scaling. Psoriasis often affects the tips of the elbows and knees, the scalp, the navel, and the area surrounding the genitals or anus. Approximately 10% of patients who have psoriasis also develop an associated inflammation of their joints. Usually, the more severe the skin symptoms are, the greater the likelihood a person will develop psoriatic arthritis. The cause of psoriatic arthritis is unknown it may have a combination of genetic, environmental, and immune causes.

Males and females are equally likely to suffer from psoriasis. For psoriatic arthritis, males are more likely to have the spondylitic form (in which the spine is affected), and females are more likely to have the rheumatoid form (in which many joints may be involved). Psoriatic arthritis usually develops in people aged 35-55 years. However, it can develop in people of almost any age. Psoriatic arthritis shares many features with several other arthritic conditions, such as ankylosing spondylitis, reactive arthritis, and arthritis associated with Crohn's disease and ulcerative colitis. All of these conditions can cause inflammation in the spine and joints, in the eyes, skin, mouth, and various organs.

According to another embodiment, the compositions, as well as the methods of the invention may be used for the treatment and/or amelioration of ankylosing spondylitis. Ankylosing spondylitis (AS, previously known as Bechterew's disease, Bechterew syndrome, Marie Strumpell disease and a form of spondyloarthritis), is usually a chronic and progressive form of arthritis, caused due to inflammation of multiple joints, characteristically the spinal facet joints and the sacroiliac joints at the base of the spine. While ankylosing spondylitis tends to affect these joints and the soft tissues around the spine, other joints may also be affected, as well as tissues surrounding the joints (entheses, where tendons and ligaments attach to bone). Ankylosing spondylitis may also involve areas of the body other than the joints, such as the eyes, heart, and lungs.

This disorder frequently results in bony ankylosis (or fusion), hence the term ankylosing, which is derived from the Greek word ankylos, meaning stiffening of a joint. Spondylos means vertebra (or spine) and refers to inflammation of one or more vertebrae.

The disease is estimated to affect approximately 0.1-0.2% of the general population. Ankylosing spondylitis primarily affects young males. Males are four to ten times more likely to have ankylosing spondylitis than females. Most people with the disease develop it at age 15-35 years, with an average age of 26 years at onset.

Although the exact cause is unknown, ankylosing spondylitis is believed to be due to the combination of a genetic influence and a triggering environmental factor. Approximately 90-95% of patients with ankylosing spondylitis have the tissue antigen Human Leukocyte Antigen B27 (HLA-B27), compared to 7% in the general population. People with ankylosing spondylitis often have a family history of the disease.

In yet another embodiment, the compositions, as well as the methods of the invention may be used for the treatment and/or amelioration of reactive arthritis (ReA). Reactive arthritis, another type of seronegative spondyloarthropathy, is an autoimmune condition that develops in response to an infection in another part of the body. Coming into contact with bacteria and developing an infection can trigger reactive arthritis. It has symptoms similar to various other conditions collectively known as "arthritis," such as rheumatism. It is caused by another infection and is thus "reactive", i.e., dependent on the other condition. The "trigger" infection has often been cured or is in remission in chronic cases, thus making determination of the initial cause difficult.

The symptoms of reactive arthritis very often include a combination of three seemingly unlinked symptoms, an inflammatory arthritis of large joints, inflammation of the eyes (conjunctivitis and uveitis), and urethritis. It should be indicated that ReA is also known as Reiter's syndrome, after German physician Hans Reiter, it is also known as arthritis urethritica, venereal arthritis and polyarteritis enterica.

It should be appreciated that there are many other forms of inflammatory arthritis, including juvenile idiopathic arthritis, gout and pseudo gout, as well as arthritis associated with colitis or psoriasis. It should be therefore appreciated that the compositions, as well as the methods of the present invention are also applicable for these conditions as well.

Therefore, according to another embodiment, the compositions and methods of the invention may be used for the treatment and/or amelioration of juvenile idiopathic arthritis (JIA). JIA, is the most common form of persistent arthritis in children (juvenile in this context refers to an onset before age 16, idiopathic refers to a condition with no defined cause, and arthritis is the inflammation of the synovium of a joint). JIA is a subset of arthritis seen in childhood, which may be transient and self-limited or chronic. It differs significantly from arthritis commonly seen in adults (rheumatoid arthritis), and other types of arthritis that can present in childhood which are chronic conditions (e.g. psoriatic arthritis and ankylosing spondylitis).

According to another embodiment, the compositions, as well as the methods of the invention may be used for the treatment and/or amelioration of gout. Gout (metabolic arthritis) is a disease created by a buildup of uric acid. In this condition, crystals of monosodium urate or uric acid are deposited on the articular cartilage of joints, tendons and surrounding tissues. These crystals cause inflammation and pain, both severe. If untreated, the crystals form tophi, which can cause significant tissue damage. Pseudo gout is a condition which is caused by calcium crystals. When calcium crystals cause attacks of inflammation in tendons it is called 'calcific tendinitis'. The invention further provides compositions and methods for the treatment of this disorder as well.

Generally, as also disclosed above, there are many types of arthritis, it should be noted that the compositions, as well as methods, combined compositions and kits of the invention may be also applicable for treating in addition to all primary forms of arthritis indicated, also to all secondary forms of arthritis. These conditions may include lupus erythematosus, Henoch-Schönlein purpura, psoriatic arthritis, reactive arthritis, haemochromatosis, hepatitis, Wegener's granulomatosis (and many other vasculitis syndromes), Lyme disease, familial mediterranean fever, hyperimmunoglobulinemia D with recurrent fever, TNF receptor associated periodic syndrome and inflammatory bowel disease (including Crohn's Disease and ulcerative colitis).

According to a specific embodiment, treatment, prevention or improvement in arthritis may be reflected in improvement in clinical score and histo-pathological score. More specifically, it should be appreciated that treatment with the compositions and method as of the invention may reduce at least one of arthritis clinical score and histo-pathological score by at least 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 5% to 35%, 5% to 30%, 5% to 25%, 5% to 20%, 5% to 15% or about 5% to 10%. More specifically, such reduction may be of at least 5%, at least 10%, at least 15%, at least 20%, at least 25%, at least 30%, at least 40%, at least 50% or even by at least 55 or 60% as compared to the clinical score prior to treatment.

It should be appreciated that the methods and compositions of the invention are applicable in the treatment of any immune-related disorder. Thus, in another specific embodiment, the pharmaceutical compositions, as well as the methods of the invention may be applicable for treating and ameliorating inflammatory bowel disease (IBD), for example, colitis and Crohn's disease. According to a specific embodiment, treatment, prevention or improvement in colitis or in Crohn's disease may be reflected in improvement in clinical score and histo-pathological score. For example, treatment with the CAP1-binding compound of the invention, that may be an anti-CAP1 antibody, may reduce at least one of IBD clinical score and histo-pathological score by at least 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 5% to 35%, 5% to 30%, 5% to 25%, 5% to 20%, 5% to 15% or about 5% to 10%. More specifically, such reduction may be of at least 5%, at least 10%, at least 15%, at least 20%, at least 25%, at least 30%, at least 40%, at least 50% or even by at least 55 or 60% as compared to the clinical score prior to treatment.

Inflammatory bowel diseases (IBD) are common gastrointestinal disorders that can be perceived as being the result of a dysbalance between Th1-pro-inflammatory, Th1-pro-inflammatory and Th2-anti-inflammatory subtypes of immune responses.

Crohn's disease is an ongoing disorder that causes inflammation of the digestive tract, also referred to as the gastrointestinal (GI) tract. Crohn's disease can affect any area of the GI tract, from the mouth to the anus, but it most commonly affects the lower part of the small intestine, called the ileum. The swelling extends deep into the lining of the affected organ. The swelling can cause pain and can make the intestines empty frequently, resulting in diarrhea.

As indicated above, Crohn's disease is an inflammatory bowel disease, the general name for diseases that cause swelling in the intestines. Because the symptoms of Crohn's disease are similar to other intestinal disorders, such as irritable bowel syndrome and ulcerative colitis, it can be difficult to diagnose. Ulcerative colitis causes inflammation and ulcers in the top layer of the lining of the large intestine. In Crohn's disease, all layers of the intestine may be involved, and normal healthy bowel can be found between sections of diseased bowel. Crohn's disease may also be called ileitis or enteritis.

It should be noted that the compositions of the invention may be also applicable for the treatment or prevention of colitis. Ulcerative Colitis (U.C.) is a chronic (long lasting) inflammation of the lining of the colon (large bowel) and rectum. The lining becomes inflamed and ulcerated. The inflammation may be limited to the rectum (proctitis) or affect the whole of the colon and rectum.

Thus, the compositions of the invention may reduce clinical score by at least 5%, at least 10%, at least 15%, at least 20%, at least 25%, at least 30%, at least 40%, at least 50% or even by at least 55 or 60% as compared to the clinical score prior to treatment.

According to another specific embodiment, the compositions, as well as the methods of the invention may be used for the treatment and/or amelioration of an autoimmune disorder, such as diabetes.

Diabetes mellitus, is a syndrome characterized by disordered metabolism and inappropriately high blood sugar (hyperglycaemia) resulting from either low levels of the hormone insulin or from abnormal resistance to insulin's effects coupled with inadequate levels of insulin secretion to compensate. The characteristic symptoms are excessive urine production (polyuria), excessive thirst and increased fluid intake (polydipsia), and blurred vision; these symptoms are likely absent if the blood sugar is only mildly elevated.

There are three main forms of diabetes: type 1, type 2 and gestational diabetes (occurs during pregnancy). Type 1 diabetes mellitus is characterized by loss of the insulin-producing beta cells of the islets of Langerhans in the pancreas, leading to a deficiency of insulin. The main cause of this beta cell loss is a T-cell mediated autoimmune attack. There is no known preventative measure that can be taken against type 1 diabetes. Most affected people are otherwise healthy and of a healthy weight when onset occurs. Sensitivity and responsiveness to insulin are usually normal, especially in the early stages. Type 1 diabetes can affect children or adults and was traditionally termed "juvenile diabetes" as it represents a majority of cases of diabetes affecting children.

The principal treatment of type 1 diabetes, even from the earliest stages, is replacement of insulin combined with careful monitoring of blood glucose levels using blood testing monitors. Without insulin, diabetic ketoacidosis can develop and may result in coma or death. Emphasis is also placed on lifestyle adjustments (diet and exercise) though these cannot reverse the loss. Apart from the common subcutaneous injections, it is also possible to deliver insulin by a pump, which allows continuous infusion of insulin 24 hours a day at preset levels, and the ability to program doses (a bolus) of insulin as needed at meal times.

Type 1 treatment must be continued indefinitely. Treatment does not impair normal activities, if sufficient awareness, appropriate care, and discipline in testing and medication are taken.

The prevalence rate in the USA is 0.12% of the population or nearly 340,000 people. The incidence rate is about 30,000 annual cases, 0.01% of the population.

According to certain embodiments, the compositions and methods of the invention may be for use in the treatment and the prevention of multiple sclerosis (MS).

Multiple sclerosis (abbreviated MS, formerly known as disseminated sclerosis or encephalomyelitis disseminata) is a chronic, inflammatory, demyelinating disease that affects the central nervous system (CNS). Disease onset usually occurs in young adults, is more common in women, and has a prevalence that ranges between 2 and 150 per 100,000 depending on the country or specific population.

MS affects the neurons in the areas of the brain and spinal cord known as the white matter. These cells carry signals in between the grey matter areas, where the processing is done, and between these and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. The name multiple sclerosis refers to the scars (scleroses—better known as plaques or lesions) in the white matter. Loss of myelin in these lesions causes some of the symptoms, which vary widely depending upon which signals are interrupted. However, more advanced forms of imaging are now showing that much of the damage happens outside these regions. Almost any neurological symptom can accompany the disease.

MS takes several forms, with new symptoms occurring either in discrete episodes (relapsing forms) or slowly accumulating over time (progressive forms). Most people are first diagnosed with relapsing-remitting MS but develop secondary-progressive MS (SPMS) after a number of years. Between episodes or attacks, symptoms may go away completely, but permanent neurological problems often persist, especially as the disease advances.

Although much is known about the mechanisms involved in the disease process, the cause remains elusive. The theory with the most adherents is that it results from an autoimmune reaction. The disease does not have a cure, but several therapies have proven helpful. Treatments attempt to return function after an episode, prevent new attacks, and prevent disability. As with any treatment, medications have several adverse effects, and many therapies are still under investigation.

According to a specific embodiment, treatment, prevention or improvement in MS disease or symptoms may be reflected in improvement in clinical score. For example, treatment with the CAP1-binding compound of the invention, that may be an anti-CAP1 antibody, may reduce at least one of MS clinical score and histo-pathological score by at least 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 5% to 35%, 5% to 30%, 5% to 25%, 5% to 20%, 5% to 15% or about 5% to 10%. More specifically, such reduction may be of at least 5%, at least 10%, at least 15%, at least 20%, at least 25%, at least 30%, at least 40%, at least 50% or even by at least 55 or 60% as compared to the clinical score prior to treatment.

It should be appreciated that the methods and compositions of the invention may be applicable for the treatments of any immune-related disorder as disclosed herein before.

Figure 28:
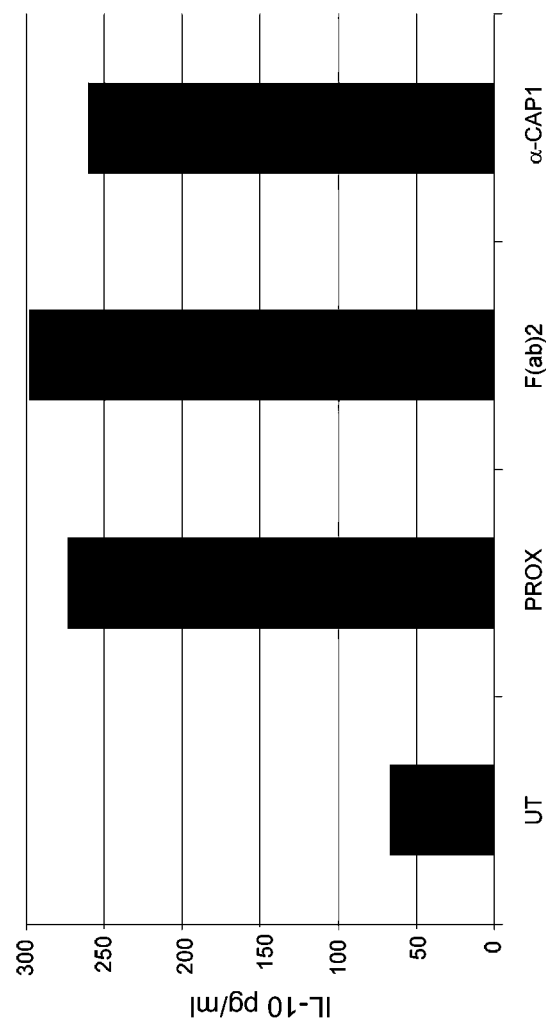

As disclosed by the following Examples, two different antibodies that were shown to interact with the CAP1 molecule, the anti-CAP1 and the anti-peptide-6 antibodies used by the invention clearly exhibit an anti-inflammatory effect. More specifically, FIG. 28 shows that exposure of human PBMCs to anti-CAP1 antibodies, anti-peptide-6 humanized antibody and F(ab)$_2$ fragment thereof, elicit sequential events resulting eventually in the up-regulation of the IL-10 gene expression. The increase of IL-10 secretion in the inflammatory site can divert the local cytokine profile from an inflammatory to an anti-inflammatory response and thus may explain the mechanism of protection against inflammation rendered by these antibodies.

Thus, CAP1-binding compounds, specifically, the antibodies used by the invention, may be used as immunomodulators, modulating the Th1/Th2 cell balance towards an anti-inflammatory Th2 response. Therefore, the invention further provides compositions and methods for increasing the expression and levels of IL-10 (Interleukin-10). According to this aspect, the compositions and methods of the invention involves the use, of an effective amount of at least one compound that interacts and binds CAP1, specifically, isolated and purified anti-CAP1 antibodies. The composition of the invention may optionally comprise a pharmaceutically acceptable carrier, excipient or diluent.

According to one embodiment, wherein indicate "increasing" or "enhancing" the expression or the levels of an anti-inflammatory cytokine, specifically of IL-10, it is meant that such increase or enhancement may be an increase or elevation of between about 10% to 100%, 20% to 80%, 30% to 70% or 40 to 60% of the expression of such cytokines. Particularly, an increase of 10%, 15%, 20%, 25%, 30%, 35%, 40%, 45%, 50%, 55%, 60%, 65%, 70%, 75%, 80%, 85%, 90%, 95% or 100% of the expression as compared to a suitable control. It should be further noted that increase or elevation may be also an increase of about 2 to 100 folds. More specifically, an increase of about 10, 15, 20, 25, 30, 35, 40, 45, 50, 55, 60, 65, 70, 75, 80, 85, 90, 95, 97 folds or more. Still further, it should be appreciated that the increase of the levels or expression of said IL-10 cytokine may be either in the transcription, translation or the stability of said cytokine.

As indicated above, the enhanced expression of IL-10 may modulate the Th1/Th2 balance towards the Th2 anti-inflammatory response. Therefore, the CAP1-binding compound used by the invention, specifically, the anti-CAP1 antibodies may be useful in conditions where modulation of the Th1/Th2 balance towards an anti-inflammatory reaction is desired. Thus, according to one embodiment, the compositions of the invention may be used for increasing the expression and levels of IL-10 in a subject in need thereof, thereby modulating the Th1/Th2 cell balance towards an anti-inflammatory Th2 response in the treated subject. According to one specific embodiment, such subject is a subject suffering of an immune-related disorder. For example, an immune-related disorder such as an autoimmune disease, (for example, arthritis, IBD, type-1 diabetes, multiple sclerosis (MS), lupus, Graves disease and thyroiditis), graft rejection pathology and graft versus host disease, and disorders induced by super antigens, such as toxic shock, septic shock and severe sepsis.

It should be further appreciated that in general, the composition as well as the methods of the present invention may be used in the treatment of any autoimmune disease such as for example, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pemphigoid, dermatitis herpetiformis, insulin dependent diabetes, inflammatory bowel disease, ulcerative colitis and Crohn's disease.

In another aspect, the invention relates to the use of a therapeutically effective amount of at least one of: (a) a compound that interacts with Adenylyl Cyclase-Associated Protein (CAP1) and/or of (b) CAP1 or any fragment, variant, derivative, homologue and mutant thereof; or any combination thereof, in the preparation of a composition for the treatment, amelioration, prevention and inhibition of immune-related disorders.

In some specific embodiments, the invention encompasses the use of a compound that specifically interacts and binds CAP1, thereby modulating the balance between Th1/Th2 in the subject, for the preparation of an immuno-modulatory composition.

In specific embodiments, an anti-CAP1-antibody that specifically recognizes and binds CAP1, thereby modulating the balance between Th1/Th2 towards the Th2 anti-inflammatory response in the subject, may be used by the invention.

It should be noted that the anti CAP1 antibodies used by the method of the invention may be any one of polyclonal and monoclonal antibodies. The term "antibody" is meant to include intact molecules as well as fragments thereof, such as, for example, Fab and F(ab)$_2$, which are capable of binding antigen.

It should be further appreciated that according to certain embodiments, any CAP1 binding compound and specifically any CAP1 binding compound that is an antibody that may be any anti-CAP1 antibody, or any antibody that recognizes and binds CAP1, other than, or with the proviso that the antibody is not any of a polyclonal, monoclonal rat or mouse anti-peptide-6 antibody (for example, antibodies designated B24 or F9 monoclonal) or any chimeric or humanized antibody derived therefrom chimeric antibody.

In other embodiments, the invention encompasses the use of CAP1 or any fragment, variant, derivative, homologue and mutant thereof, in the preparation of a composition for the treatment of immune-related disorders by modulating the balance between Th1/Th2 in the subject.

In a fifth aspect, the invention provides Adenylyl Cyclase-Associated Protein (CAP1) or any fragment, variant, derivative, homologue and mutant thereof, that modulates the balance between Th1/Th2 in a subject in need thereof, for use in the treatment of an immune-related disorder in the subject.

It should be further noted that wherein said CAP1 molecule or any fragment thereof used herein may be provided as any one of a purified recombinant protein, and a cell lysate or membrane preparation of a transformed host cell expressing the CAP1 molecule. The terms fragments and functional fragments used herein mean the CAP1 molecule or any fragment thereof, with any insertions, deletions, substitutions and modifications, that is capable of inducing specific modulation of the Th1/Th2 cell balance (hereafter referred to as "fragment/s"), as reflected by activation of Th2 anti-inflammatory cytokines, for example, IL-10, or alternatively, Th1 pro-inflammatory cytokines. It should be appreciated that according to certain embodiments as used herein in the specification and in the claim section below, the CAP1 protein refer to human CAP1 protein comprising the amino acid sequence as denoted by GenBank Accession No. NP_001099000.1, shown by FIG. 30 and also denoted as SEQ ID NO.:6 and encoded by the human CAP1 gene as shown by GenBank Accession No. CAG33690.1.

The invention also provides an anti-CAP1-antibody that specifically recognizes and binds CAP1, thereby modulating the balance between Th1/Th2 towards the Th2 anti-inflammatory response in a subject in need thereof, for use in the treatment of an immune-related disorder in the subject.

As indicated above, the results disclosed by the present invention clearly demonstrate the role of CAP1 as a key element in this immuno-modulatory pathway and therefore as a potential target for immuno-modulation. The invention therefore provides the use of CAP1 as a target for searching of immuno-modulating compounds. Thus, in a further aspect, the invention relates to a screening method for an immuno-modulating compound which modulates the Th1/Th2 cell balance in a subject in need thereof. The screening method of the invention comprises the steps of: (a) obtaining a candidate compound which binds to Adenylyl Cyclase-Associated Protein (CAP1) or to any fragment, variant, derivative, homologue and mutant thereof; and (b) determining the effect of the compound obtained in step (b), on modulation of the Th1/Th2 balance, specifically by examining either anti-inflammatory or pro-inflammatory cytokine expression. Whereby modulation of an anti-inflammatory or pro-inflammatory cytokine expression by said candidate compound is indicative of the ability of said compound to modulate the Th1/Th2 balance.

The term "candidate compound" is meant to refer to any compound wherein the characterization of the compound's ability to bind CAP1 and thereby modulate Th1/Th2 balance is desired. "Modulate" is intended to mean an increase, decrease, or other alteration of any or all cytokines, lymphokines and any cellular processes related to immune responses. In this regard an alteration may include a preference for an increase in IL-10 expression and the modulation of Th1/Th2 balance towards a Th2 immune response.

Key to the application of high-throughput screening for high-affinity binding of immuno-modulating compounds to the CAP1 molecule is the development of a sensitive and convenient screening assay.

Development of a robust screening assay for immuno-modulating compounds through their affinity for CAP1 will be the first step in said screening method.

Therefore, the candidate immuno-modulating compound may be obtained by the steps of: (a) providing a mixture comprising the CAP1 molecule or any fragment, variant, derivative, homologue and mutant thereof; (b) contacting the mixture with a candidate compound under suitable conditions for said binding; and (c) determining the effect of the candidate compound on an end-point indication. It should be noted that modulation of the end point indicates the binding of CAP1 molecule to the tested candidate compound.

According to one specific embodiment, the end point indication may be the binding of an anti-CAP1 antibody to the CAP1 molecule, which leads to a visually detectable signal. In such case, an increase in this end point is indicative of binding of said test compound to the CAP1 molecule.

The term "detectable" as used herein refers to the presence of a detectable signal generated from a detectable chemical reaction that is immediately detectable by observation, instrumentation, or film.

More specifically, the term "detectable signal" as used herein refers to a signal causing an occurrence of, or a change in, a signal that is directly or indirectly detectable (observable) either by visual observation or by instrumentation. Typically, the detectable signal is detectable in an optical property ("optically detectable") as reflected by a change in the wavelength distribution patterns or intensity of absorbance or fluorescence or a change in light scatter, fluorescence lifetime, fluorescence polarization, or a combination of such parameters.

More particularly, each candidate compound, that may be for example, a peptide or any small molecule, may be placed in a well and direct binding of the CAP1-molecule or any fragments thereof, is detected, preferably by an antibody specific for CAP1. Conditions for effective binding of the CAP1 molecule or any fragments thereof to a candidate immuno-modulating compound on the plate may be optimized involving study of pH, salt and buffer composition, and carrier proteins such as BSA. This robust screening yields compounds that bind to the CAP1 molecule. Such compounds that bind to the CAP1 are pooled and then assayed as described below.

It should be noted that the anti CAP1 antibody used by the methods of the invention may be any one of polyclonal and monoclonal antibody. It should be further noted that the term "antibody" is meant to include intact molecules as well as fragments thereof, such as, for example, Fab and $F(ab')_2$, which are capable of binding antigen.

According to certain embodiments, in a further optional step of the screening method of the invention, the candidate immuno-modulating compounds which bind CAP1, and were obtained as described above, may be further selected for their ability to specifically bind CAP1 at the anti-peptide-6 antibody binding site within the CAP1 molecule. Such selected compounds will desirably be capable of preventing or modulating the interaction between said CAP1 and anti-peptide-6 antibody. According to this specific embodiment, the optional selection may be performed by the steps of: (a) providing a mixture comprising a CAP1 molecule or any fragment, variant, derivative, homologue and mutant thereof; (b) contacting said mixture with the tested candidate compound under suitable conditions for specific interaction of the anti-peptide-6 antibody with the CAP1 molecule via the anti-peptide-6 binding site; and (c) determining the effect of the tested candidate compound on an end-point indication. Modulation of such end point is indicative of binding of the tested candidate compound to the CAP1 molecule via said anti-peptide-6 binding site.

According to another embodiment, the mixture used for the optional selection stage comprises: (a) CAP1 molecule or any fragment, variant, derivative, homologue and mutant thereof; (b) an anti-petide-6 antibody which specifically binds to CAP1 molecule, via the anti-peptide-6 binding site in CAP1; and (c) optionally solutions, buffers and compounds which provide suitable conditions for interaction of the anti-peptide-6 antibody with the CAP1 molecule and for the detection of an end-point indication for the interaction. According to one embodiment, the end point indication may be the binding of the anti-peptide-6 antibody to the CAP1 molecule, which leads to a visually detectable signal.

In a further embodiment of the invention, an inhibition observed in such end point indicates direct binding of the tested candidate compound to the anti-peptide-6 antibody binding site in CAP1. Accordingly, the binding of the candidate compound competes with the binding of the anti-peptide-6 antibody to the binding site and hereby modulates and/or inhibits said binding.

For performing this competition assay, the anti-peptide-6 antibody may be directly labeled, for example by biotinylation or by addition of fluorescein, or alternatively may be indirectly labeled by a secondary antibody.

The mixture used for obtaining and selecting candidate compounds by the screening method of the invention may be a cell mixture or a cell-free mixture.

According to one alternative embodiment, the mixture utilized by the method of the invention may be a cell-free mixture. Such mixture comprises the CAP1 molecule or any functional fragment thereof (preferably, comprising the anti-peptide-6 antibody binding site), that may be provided as any one of a peptide, a purified recombinant protein, a fusion protein and a cell lysate or membrane preparation of a transformed host cell expressing the said CAP1 molecule.

In a particular and non limiting example, such optional selection may be performed, where CAP1 is bound onto the wells of a microplate. Then, each well is incubated with a limiting amount of the anti-peptide-6 antibody, in the presence of the candidate immuno-modulating compound. Supernatant is collected from each well. Unbound antibody is detected in the supernatant by secondary antibody ELISA. Should the test compound bind tightly to CAP1 in the domain recognized by the ani-peptide-6 antibody, it will compete in the binding of anti-peptide-6 antibody to CAP1 and release free anti-peptide-6 antibody that can be detected over a zero background, rendering the assay sensitive. Candidate compounds binding outside the domain involved in the anti-peptide-6-antibody/CAP1 interaction will be eliminated by this approach.

An alternative approach is to use a labeled anti-peptide-6 antibody and assay for the ability of the candidate compounds to displace labeled antibody from binding to CAP1 on the plate.

Alternatively, the mixture utilized for such optional selection step, may be a cell mixture. In this particular embodiment, each candidate compound, preferably a peptide, is placed in a well and the well is then blocked with BSA or fetal calf serum. Binding of THP-1 cells, for example, that express CAP1 on their cell surface is scored visually, or by anti-CAP-1 ELISA. Alternatively, cell membranes prepared from the CAP1-expressing cells may be used, and binding is detected using anti-CAP1 antibody. Positive candidate compounds are then re-examined in the presence of the anti-peptide-6 antibody, as competitor.

It should be appreciated that wherein said anti-peptide-6 antibody is meant an antibody that specifically directed against an amino acid sequence comprising peptide 6, as denoted by the amino acid sequence of SEQ ID NO. 1. It should be noted that anti-peptide-6 antibody encompasses polyclonal, monoclonal, chimeric and humanized anti-peptide-6 antibodies, as well as F(ab) fragments thereof. It should be noted that the term Proximab as used herein is a humanized anti-peptide-6 antibody prepared by the present inventors.

It should be noted that the CAP1 molecule or any fragment thereof comprised in the mixture, may be provided as any one of a purified recombinant protein, and a cell lysate or membrane preparation of a transformed host cell expressing the CAP1 molecule. The terms fragments and functional fragments used herein mean the CAP1 molecule or any fragment thereof, with any insertions, deletions, substitutions and modifications, that include the anti-peptide-6 binding site and is capable of binding this antibody and thereby inducing specific modulation of Th1/Th2 cell balance (hereafter referred to as "fragment/s"), as reflected by activation of anti-inflammatory cytokines, such as, IL-10, or alternatively, activation of pro-inflammatory cytokines.

According to another embodiment, the candidate compound examined by the screening method of the invention may be selected from the group consisting of: protein based, nucleic acid based, carbohydrates based, lipid based, natural organic based, synthetically derived organic based, inorganic based, and peptidomimetics based compounds.

According to another embodiment, the compound may be product of any one of positional scanning of combinatorial libraries of peptides, libraries of cyclic peptidomimetics, and random or dedicated phage display libraries.

According to another specific embodiment, the second stage of the screening method of the invention involves further evaluation of the feasibility of the selected candidate compounds to actually modulate the expression of anti-inflammatory cytokines and thereby, their ability to modulate innate immunity. Therefore, the candidate compounds that were obtained, and optionally selected as described above, are next evaluated for their ability to modulate the Th1/Th2 cell balance, specifically, to activate Th2 lymphocytes. This evaluation stag involves the steps of: (a) providing a test system comprising a CAP1 molecule or any fragment, variant, derivative, homologue and mutant thereof; (b) contacting the test system with a tested candidate compound obtained and optionally selected by the previous stage of the screening method of the invention; and (c) determining the effect of the candidate compound on an end-point indication as compared to a control, wherein said effect is indicative of the ability of the tested candidate to modulate the activation of pro-inflammatory Th1 or anti-inflammatory Th2 lymphocytes.

The test system used for evaluating the candidate immunomodulating compound isolated by the screening method of the invention may be an in-vitro/ex-vivo cell culture, or an in-vivo animal model. Such test system optionally further comprises endogenous and/or exogenous compounds which provide suitable conditions for activation of Th2 cells and for the detection of an end-point indication for determining the modulatory effect of the candidate compound. More specifically, said activation or modulation is determined by the induction of Th2 cytokines such as IL-10 and/or IL-4 gene expression.

The test system utilized by the screening method of the invention for evaluation may be an in-vitro/ex-vivo cell culture comprising an endogenously expressed CAP1 molecule. In a particular example, the cell culture used as the test system may be a PBMC culture isolated from a mammalian donor.

The end point indication in this particular test system may therefore be the anti-CAP1 or the anti-peptide-6 antibody-induced expression of IL-10 and/or of IL-4, which leads to a visually detectable signal. Thus, any modulation, inhibition or even reduction of said end point is indicative of the ability of the candidate compound to specifically modulate the Th1/Th2 balance, specifically, as reflected by activation of the anti-inflammatory cytokine, IL-10 or alternatively, activation of a pro-inflammatory cytokine. The anti-peptide-6 antibody-induced expression of IL-10 may be detected, for example, by quantitative dot blot hybridization and RNAase protection assay.

It should be noted that the test system used by the invention optionally further comprises endogenous and/or exogenous compounds which provide suitable conditions for anti-inflammatory cytokine expression and for the detection of an end-point indication for determining the immunomodulatory effect of the candidate compound.

In another preferred embodiment, the modulation of expression of the anti-inflammatory cytokine may be any one of increasing or decreasing the expression of said cytokine as compared to a control.

It should be noted that according to certain embodiments, the screening method of the invention is specifically directed for identification of compounds modulating the expression of any anti-inflammatory cytokine for example, IL-10, IL-4, and IL-6. More specifically, according to some embodiments, the screening method of the invention is directed to identify compounds activating a Th2-anti-inflammatory response.

The invention also provides an immuno-modulatory compound which interacts with CAP1 and thereby modulates the Th1/Th2 cell balance in a subject in need thereof, wherein the compound is identified by the screening method according to the invention.

Finally, in a further aspect, the invention relates to a pharmaceutical unit dosage form comprising as an active ingredient a therapeutically effective amount of at least one of (a) a compound that interacts with Adenylyl Cyclase-Associated Protein (CAP1) and of (b) CAP1 or any fragment, variant, derivative, homologue and mutant thereof, or any combination thereof, for the preparation of a medicament effective in the treatment of immune-related disorders, the dosage form optionally further comprises a pharmaceutically acceptable carrier, excipient or diluent.

According to certain embodiment, the pharmaceutical unit dosage form of the invention may comprises as an active ingredient a compound that specifically interacts and binds CAP1, thereby modulating the balance between Th1/Th2 in the subject.

In yet another embodiment, such compound may be an anti-CAP1-antibody that specifically recognizes and binds CAP1, thereby modulating the balance between Th1/Th2 towards the Th2 anti-inflammatory response in the subject.

According to an alternative embodiment, the pharmaceutical unit dosage form of the invention comprises as an active ingredient CAP1 or any fragment, variant, derivative, homologue and mutant thereof, thereby modulating the balance between Th1/Th2 in the subject.

The invention will be described in more detail on basis of the following Examples, which are illustrative only and do not in any way limit the invention. Many modifications and variations of the present invention are possible in light of the present teachings. It is therefore understood, that within the scope of the appended claims, the invention may be practiced otherwise than specifically described.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Antibodies

*Mouse anti-peptide-6 antibody is a mouse monoclonal antibody developed from peptide-6-immunized Balb/C mice by the hybridoma technique and is of the IgM isotype.

*Rat anti-peptide-6 antibody is a rat monoclonal antibody developed from peptide-6-immunized Lewis rats by the hybridoma technique and is of the IgM isotype.

*Chimeric anti-peptide-6 IgG1 mouse and rat antibodies were developed by Antitope Ltd. using standard chimerization technique. The resulting chimeric antibodies are composed of either the mouse variable region from the mouse antibody or the rat variable region from the rat monoclonal antibody, and the human constant region of the IgG1 isotype.

*Humanized anti-peptide-6 antibodies based on the mouse reference antibody were produced by Antitope Ltd. using the Composite Human Antibody™ technique (described in WO 2006/082406).

FITC labeled humanized antibodies were used for the FACS analysis. In some embodiments the term Proximab may be used to describe monoclonal humanized antibodies against the peptide-6 epitope of the MT HSP65.

*CD 14-PE (Sigma);

*Anti CD32-PE conjugated (CALTAG™ Laboratories);

*Anti CD64-APC conjugated (CALTAG™ Laboratories);

*FITC-conjugated goat anti-rat IgG+IgM (Jackson ImmunoResearch Lab. Inc. West Grove, Pa. 19390, USA);

*Anti human IgG-FITC (Sigma);

*Polyclonal mouse anti-human CAP1 (Abnova Corporation, Taiwan);

Cell-Culture Conditions

*MM6-Mono Mac 6 (Human myelomonocytic cell line, DSMZ No. ACC 124).

MM6 cells were maintained in RPMI medium supplemented with 2 mM glutamine, 1 mM pyruvate, 1% non essential amino acids, 0.1% pen-strep, 10% FCS and 10 µg/ml human insulin.

*THP-1 (Human acute monocytic leukemia cell line, ATCC No. TIB-202). THP-1 cells were maintained in RPMI medium supplemented with 10% FCS, 2 mM L-Glutamine, Penicillin, Streptomycin and 10 mM HEPES (pH=7.3).

*HeLa (human cervical carcinoma cell line, ATCC No. CCL-2).

HeLa cells were maintained in DMEM medium supplemented with 10% FCS, 2 mM L-Glutamine and 0.1% pen-strep Cells were grown at 5% $CO_2$ and 37° C. incubator.

Kits

*ReadyPrep™ Protein Extraction kit (Membrane I) (Bio-Rad Laboratories, Inc., Hercules, Calif. 94547, USA).

*ReadyPrep™ Protein Extraction kit (Cytoplasmic) (Bio-Rad Laboratories, Inc., Hercules, Calif. 94547, USA).

*Dylight™ Antibody Labeling Kit (Thermo Scientific Pierce Protein Research Products, Rockford, Ill., USA).

*F(ab)$_2$ preparation kit (Thermo Scientific Pierce Protein Research Products, Rockford, Ill., USA).

*siRNA kit HiPerfect transfection Reagent (Qiagen)+All star and CAP1_5 siRNA (Qiagen)

Generation of Monoclonal Mouse and Rat Anti-Peptide-6 Producing Hybridomas (B24)

Six-weeks-old female Balb/c mice or Lewis rats were injected subcutaneously with 100 µg peptide-6 (GPKGRNV-VLEKKWGAP, as denoted by SEQ ID NO. 1) suspended in complete Freund's adjuvant. Animals were injected 2 more times with the peptide in incomplete Freund's adjuvant at 3 weeks intervals. Sera were collected for measurement of anti-peptide-6 antibody levels by ELISA and animals with the highest levels were treated with 2 consecutive intraperitoneal injections of 50 µg peptide in PBS (Phosphate buffer saline, 137 mM NaCl, 2.7 mM KCl, 10 mM sodium phosphate dibasic, 2 mM potassium phosphate monobasic, pH 7.4). On the following day spleens were fused with the BALB/c Ig-nonsecreting myeloma NSO. The presence of antibodies specifically recognizing peptide-6 was detected in the supernatants by specific ELISA, and positive clones were expanded. For this study, a clone designated B24 was used, which produced antibodies of the IgM type. These monoclonal antibodies are referred to as anti-peptide-6. Anti-peptide-6 antibodies were purified from the supernatants of hybridoma cells. Purification was performed by thioadsorption followed by protein G chromatography (Adar Biotech, Israel). The purity of antibodies was confirmed by SDS-PAGE.

Generation of Chimeric Anti-Peptide-6 Antibodies mRNA was extracted from B24 cells (Promega Catalogue No. Z5400). RT/PCR was performed using degenerate primer pools for murine signal sequences with a single constant region primer. Heavy chain variable region mRNA was amplified using a set of six degenerate primer pools and light chain variable region mRNA was amplified using a set of eight degenerate primer pools. Each product was cloned and several clones from each sequenced. For both antibodies, single functional heavy and light chain variable region sequences were identified. The B24 variable regions were transferred to an expression vector system (Antitope Ltd.) for both IgG1 and IgG4 heavy chains.

Preparation of Humanized Anti-Peptide-6 Antibody

Humanized anti-peptide-6 antibodies, herein referred to as Proximab, were produced by Antitope Ltd. using the Composite Human Antibody™ technique (described in WO 2006/082406), based on the chimeric mouse reference antibody.

Briefly, segments of human variable region (V region) sequence were sourced from unrelated human antibody sequence databases. Each selected sequence segment (as well as the junctions between segments) were tested for the potential to bind to MHC class II using iTope™ analysis, and all final Composite Human Antibody™ sequence variants were designed to avoid T cell epitopes. Composite Human Antibody™ V (variable) region genes were generated using synthetic oligonucleotides encoding combinations of the human sequence segments. These were then cloned into vectors containing human constant regions, and the antibodies were produced and tested for binding to target antigens by competition ELISA. The resulting antibody variants combining VH1-4 (variable heavy chains 1-4) with VK1-3 (variable light chains 1-3) were designated accordingly, for example, VH1/VK1, VH2/VK1 etc. It should be also noted that these variants are also indicated as Proximab.

Preparation of F(ab)$_2$ Fragment of Humanized Anti-Peptide-6 Antibody

F(ab)$_2$ fragments of the humanized VH2/VK3 variant anti-peptide-6 antibody (Proximab) were generated using F(ab)$_2$ preparation kit by pepsin digestion (according to the manufacturers' instructions). F(ab)$_2$ fragments were labeled with FITC (Fluorescein isothiocyanate, Sigma) using Dylight™ Antibody Labeling Kit (Pierce; according to the manufacturers' instructions).

Preparation of Human Peripheral Blood Mononuclear Cells

Human venous blood was collected from a healthy volunteer or from buffy coat obtained from the blood bank (containing fraction of an anticoagulated blood sample after density gradient centrifugation that contains most of the white blood cells, red cells and platelets). Blood was layered on a Ficol gradient (Ficoll Hypaque TM-GE Healthcare) to separate and enrich the white blood cell fraction. Cells were centrifuged at 1800 rpm for 30 minutes at room temperature. The mononuclear band was extracted and re-suspended in PBS to a final volume of 40 ml, and centrifuged at 1100-1200 rpm for 10 minutes. The pellet was suspended in RPMI supplemented with 2% human serum, 2 mM glutamine, 100 µg/ml streptomycin, 100 U/ml penicillin (all reagents from Biological Industries, Beit-Haemek, Israel). Cells were seeded in 24-well plates at a concentration of $1-2 \times 10^6$. In cases which only adherent cells were desired, the cells were incubated for 1.5-3 hrs (37° C., 7% $CO_2$) and then non-adherent cells were washed out four times with PBS.

CD14+ cells were further isolated from the mixture with anti-human CD14 magnetic beads (BD Biosciences Pharmingen) according to the manufacturer's instructions.

Fluorescence-Activated Cell Sorting (FACS) Analysis $10^6$ CD14+ cells, $10^6$ MM6 cells or $0.5*10^6$ THP-1 cells were incubated with primary antibodies diluted in 1% BSA, 1% goat serum in PBS (FACS medium) for 1 hour at 4° C. The cells were washed twice with FACS medium and incubated with 250 ng/tube FITC-conjugated goat anti-rat IgG+IgM (Jackson ImmunoResearch Lab. Inc. West Grove, Pa. 19390, USA) diluted in FACS medium for 30 minutes at room temperature. The cells were then washed and analyzed by LSRII Flow Cytometer using FCS express 3 program (De novo software).

Staining of MM6 Cells with Chimeric Anti-Peptide-6 Antibody

Mono Mac 6 (MM6) cells were stained with 10 µg chimeric (CHM) anti-peptide-6 antibody followed by 1:200 secondary anti human IgG-FITC, alone or together with 1:20 mouse-anti-human CD14-APC (Miltenyi Biotec). The cells were fixed with 3.7% Formaldehyde, placed on slides, covered with mounting buffer, and viewed under Zeiss confocal microscope.

Affinity Chromatography

Sepharose-beads were bound to mouse and rat anti-peptide-6 monoclonal antibodies (5 mg antibody/2 ml sepharose) and columns constructed. THP-1 human promonocytic hydrophilic membranes proteins were added with Tween 20 to 0.1. After removal of solid material, samples were loaded on the columns. Elution was done under acidic conditions (0.1N Glycine pH 2.4), followed by high salt (3.2M Na Isothiocynate). 1.5 ml fractions were collected and protein content was detected using Bradford protein detection method. Pellets were suspended in PBS and dialyzed ×3 against PBS.

Western Blot Analysis

THP-1 proteins fractions (Example 4), THP-1 promonocytes hydrophilic membrane proteins (20 µg) eluted from anti-peptide-6 affinity chromatography column, and *Mycobacterium tuberculosis* (MT) Heat Shock Protein 65 (5 µg), were boiled and resolved on 9% SDS polyacrylamide electrophoresis gel following by transfer to Nitrocellulose membrane using electric power. Western blot was carried out using rat anti-peptide-6 monoclonal antibody B24. The binding intensity was detected by goat anti-rat Fc Peroxidase (HRP) followed by incubation with HRP substrate and chemiluminescence signal detection.

Reverse-Transcription Polymerase Chain Reaction (RT-PCR)

Total RNA was extracted by SV Total RNA Isolation System (Promega, USA) and cDNA was prepared with Reverse Transcription System (Promega, USA). The resulting cDNA was amplified by PCR with the following primers:

```
IL-10:
upstream - 5' ACCAAGACCCAGACATCAAG 3',;
(also denoted by SEQ ID NO. 2)

downstream - 5' GAGGTACAATAAGGTTTCTCAAG 3',;
also denoted by SEQ ID NO. 3)

GAPDH:
upstream - 5' CCCATCACCATCTTCCAGGAGCG 3';
also denoted by SEQ ID NO. 4)

Downstream - 5' CATGCCAGTGAGCTTCCCGTTCA 3'.
also denoted by SEQ ID NO. 5)
```

The primers yielded products of 461 bp and 476 bp for the IL-10 and GAPDH mRNAs, respectively.

Electro Mobility-Shift Assay (EMSA)

Nuclear extracts were prepared as previously described [Lee, K. et al. Gene. Anal. Technol. 5:22-31 (1988)]. Oligonucleotides were labeled in a 20 µl reaction mixture containing 20 ng of double stranded oligonucleotide, 1 µl Klenow DNA polymerase and 5 µl of 10 µC/µL [$\alpha$-$^{32}$P] dCTP (Amersham, UK). In a final volume of 20 µl, 200 pg of labeled oligonucleotides were incubated at 30° C. for 40 min, with the nuclear extracts (10 µg protein) in a buffer containing 12 mM HEPES pH 7.2, 60 mM KCl, 0.6 mM $Na_2$EDTA, 0.6 mM DTT, 5 mM $MgCl_2$ and 1 µg poly d(I-C). The reaction mixtures were electrophoresed on 4% polyacrylamide gels in 0.5 TBE buffer, 200V for 90 min.

siRNA Interference of CAP1 Expression

Human THP-1 promonocytic cells were seeded on 24-well plates at a concentration of 60,000 cells/100 microliter RPMI Medium. 5 picomoles of All star negative siRNA or 5 picomoles of CAP1 siRNA were diluted in 100 microliters RPMI Medium without serum, containing 3 microliters HiPerfect transfection Reagent (Qiagen). After 10 minutes of incubation, the siRNA solution was added to the cells. The cells were incubated for 6 hours in 37° C., 7% $CO_2$ following by addition of 400 microliters of RPMI Medium. After 48 hours of incubation in the same conditions, cells were harvested, and subjected to Fluorescence-Activated Cell Sorting (FACS) analysis as described above.

ELISA—Evaluation of Cytokine Levels

Evaluation of cytokine levels in cell culture or in the serum of animals was carried out utilizing specific kits from R&D SYSTEMS, Minneapolis Minn. USA (according to the manufacturer's instructions).

Induction and Clinical Assessment of Adjuvant-Induced Arthritis

Six to eight week old female inbred Lewis rats (Harlan Laboratories, Israel) were injected intradermally at the base of the tail with 1 mg of *Mycobacterium tuberculosis* (MT) H37Ra (Difco, Detroit, Mich.) in CFA (Difco). Severity of arthritis (arthritis index) was assessed every other day by a blinded observer as follows: 0, no arthritis; 1, redness of the joint; 2, redness and swelling of the joint. The ankle and tarsal-metatarsal joints of each paw were scored. A maximum score of 16 can be obtained.

Example 1

Figure 1:
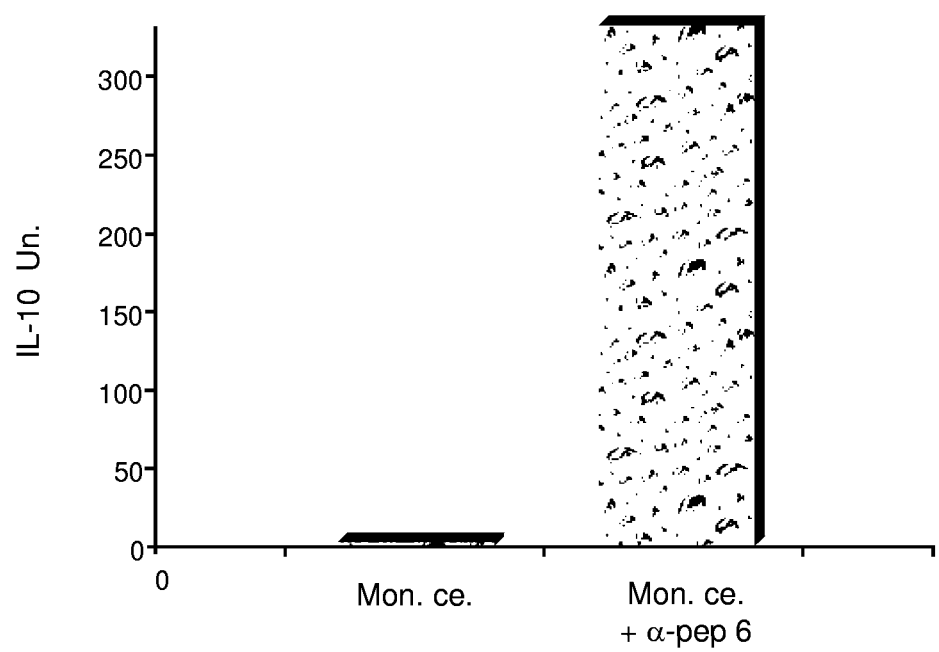
FIG. 1

Anti-Peptide-6 Antibodies Induce Transient Up-Regulation of IL-10-Specific mRNA, IL-10 Secretion and Alleviate Adjuvant Arthritis The molecular mechanism of action of HSP-65 peptide-6 binding antibodies was investigated. The effects of murine anti-peptide-6 mAbs on monocytes were evaluated in vitro and shown to induce a significant secretion of the anti-inflammatory cytokine IL-10 by human monocytes. Naïve human monocytes were incubated (24 h, 37° C., 5% $CO_2$) in RPMI with murine anti-peptide-6 mAb, and IL-10 secretion to the medium was measured by ELISA. Untreated cells served as a control. FIG. 1 shows the induction of IL-10 by murine monoclonal anti-peptide-6. Similar results have been obtained with the humanized Proximab (not shown).

The inventors next examined the effect of anti-peptide-6 antibodies on IL-10 transcriptional activity, and therefore the effect of the B24 rat anti-peptide-6 antibodies on IL-10 mRNA levels was tested in vitro. Human monocyte cells (PBMC) were incubated with either the B24 anti-peptide-6 monoclonal antibody, total naïve Lewis IgM antibodies as a negative control or lipopolysaccharide (LPS) as a positive control. The cells were harvested after 4 and 24 hours following exposure to LPS, total naïve Lewis IgM control or B24. The extracted RNA was tested by reverse transcription-PCR (RT-PCR) for IL-10 mRNA (FIG. 2A). GAPDH cDNAs were used as control for equal loading (FIG. 2B). As shown in FIG. 2A, both LPS and the anti-peptide-6 antibody induced an increase in IL-10 mRNA four hours post-exposure, compared to the untreated and naïve Lewis IgM-treated cells. However, the expression level in cells treated with anti-peptide-6 was reduced after 24 hours of incubation with the antibody, contrary to the LPS-treated cells, in which the mRNA level remained constant 24 hours post-exposure. These results suggest that anti-peptide-6 induces an up-regulation of IL-10 mRNA expression, which is transient.

Figure 3:
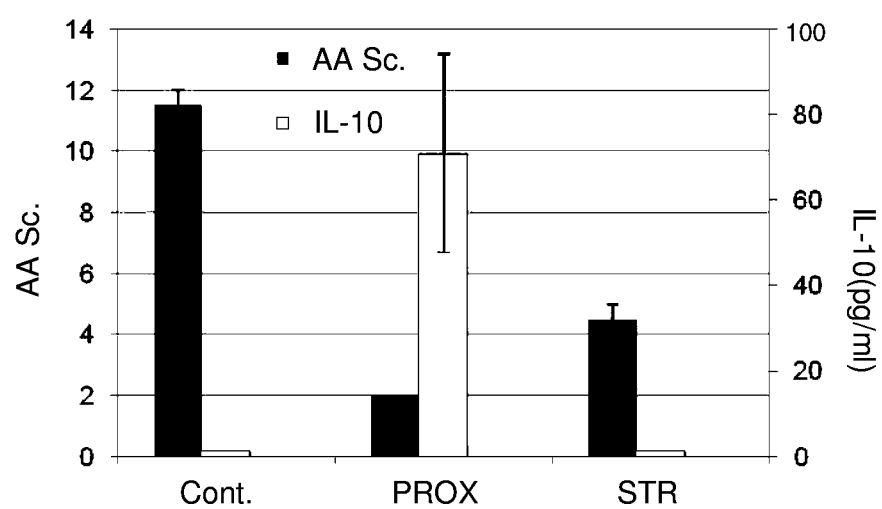

The effects of Proximab (humanized anti-peptide-6 mAb) on induction of IL-10 levels in an experimental model of established arthritis were next evaluated. Lewis rats were immunized on day 0 with MT in CFA to induce arthritis, and arthritis severity was measured via clinical scoring. Animals were treated with either PBS (negative control), steroids or Proximab. As demonstrated in FIG. 3, Proximab was shown to be effective in reducing the severity of adjuvant arthritis in mice as compared to vehicle (PBS) treated negative controls, and these animals were shown to have high levels of IL-10. Steroids were also effective at reducing the severity of arthritis, however they did not show a mechanism of induction of IL-10 secretion.

Example 2

Anti-Peptide-6 Antibodies Bind to Human CD14+ Cells

The goal of the present invention was to identify the target protein of the anti-peptide-6 antibody and to characterize the intracellular processes triggered by this interaction. Without being bound by the theory, the inventor's working hypothesis is that anti-peptide-6 antibodies cross-react with a monocyte membrane ligand, activating a signal transduction pathway that leads to the increase in transcriptional activity and secretion of IL-10. To explore this hypothesis further, the inventors attempted to identify the specific target cells of the anti-peptide-6 antibody. CD14 positive cells were isolated with magnetic beads from human PBMCs and stained with either a FITC labeled chimeric anti-peptide-6 antibody (CHM, FIG. 4B), or anti-human CD14-PE (FIG. 4C), or both (FIG. 4D). Unstained cells were used as a negative control (FIG. 4A). The cells were then analyzed by FACS for the binding of the antibodies. As shown in FIG. 4D, most of the cells in the double-stained fraction were positive for both CHM and CD14+, indicating that the CHM antibody efficiently binds CD14+ cells. These results suggest that the CHM antibody specifically interacts with an extracellular component of CD14+ cells.

To ascertain whether the humanized anti-peptide-6 antibody, Proximab, binds with similar characteristics, a similar experiment was performed using Proximab instead of CHM. Human PBMC cells were isolated from a healthy donor and separated on a Ficoll gradient. The isolated cells were stained with either anti-CD14-APC conjugated (FIG. 5A) or with both FITC-labeled Proximab, and APC-anti-CD14 (FIG. 5B). The results show that Proximab binds to the CD14+ cells (monocytes constituting ~10% of the isolated cell population, FIG. 5B, upper right quadrant). FIG. 5C depicts the percent of cells out of the CD14+ population that were stained with FITC (Without Proximab—black, With Proximab—grey), showing that Proximab binds a large percent (75%) of the CD14+ population. Similar results have also been obtained with the murine anti-peptide-6 mAb.

Having shown that the antibodies bind to CD14 positive cells, the inventors further evaluated the binding of CHM to the membrane of a monocytic cell line. CD14+ Mono Mac 6 (MM6) cells, derived from a myelomonocytic cell line, were utilized for this experiment and stained with CHM antibodies, and then exposed to anti-human IgG-FITC conjugated antibodies alone or together with mouse-anti human CD14-APC. After staining, cells were fixed, placed on slides and viewed under a confocal microscope. As clearly shown in FIG. 6A, CHM antibodies specifically bind to the membrane of MM6 cells. The cells stained both with CHM-FITC (green) and CD14 (red) (FIG. 6B) reveal that the binding of the CHM antibody is dispersed throughout the membrane, similar to the staining of the CD14 antibody, indicating that the ligand of the CHM antibody is located on the membrane surface of CD14 positive cells.

Example 3

Binding of the Anti-Peptide-6 Antibody to Human Monocyte Cells is not Mediated by the Fc Receptor The inventors next examined the possible involvement of a known component of the immune system (such as the Fc receptor) as a target for the anti-peptide-6 antibodies. It has been previously reported that MM6 cells express the receptors Fc gamma RI (CD64) at about 71% and Fc gamma RII (CD32) at about 96%, but do not express the receptor Fc gamma RIII (CD16) [Tron, et al., Eur. J. Immunol, 38: 1414-1422 (2008)]. To test whether the humanized anti-peptide-6 antibody binding to MM6 cells is mediated through the Fc receptors present on these cells, the inventors used two antibodies against the Fc receptors CD32 and CD64, as well as a non-fluorescent humanized anti-peptide-6 antibody (VK3), which served as competitor to the FITC labeled humanized anti-peptide-6 antibody (VK3-FITC). The analysis was preformed by FACS.

Figure 7:
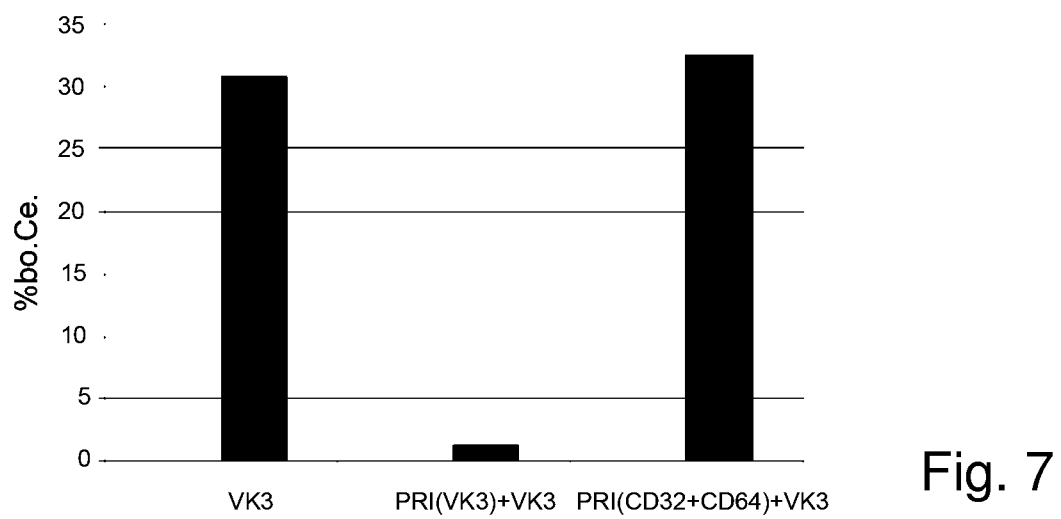

FIG. 7 presents the binding of VK3-FITC to MM6 cells after pre-incubation of the cells with non-labeled VK3, or with antibodies to CD32 and CD64. As shown, the FITC-VK3 bound to 30% of the cells (left bar). Interestingly, pre-incubation with antibodies against both Fc receptors (CD32 and CD64) did not inhibit the binding of VK3-FITC to these cells (right bar). In contrast, pre-incubation with the non-fluorescent VK3 antibody completely abolished VK3-FITC binding (middle bar). These results clearly indicate that the humanized anti-peptide-6 antibody does not utilize the Fc receptors presented on the MM6 cells, but rather targets a different membrane protein.

Example 4

Anti-Peptide-6 Antibody Binds to a Monocyte Hydrophilic Membrane Protein

Figure 8A:
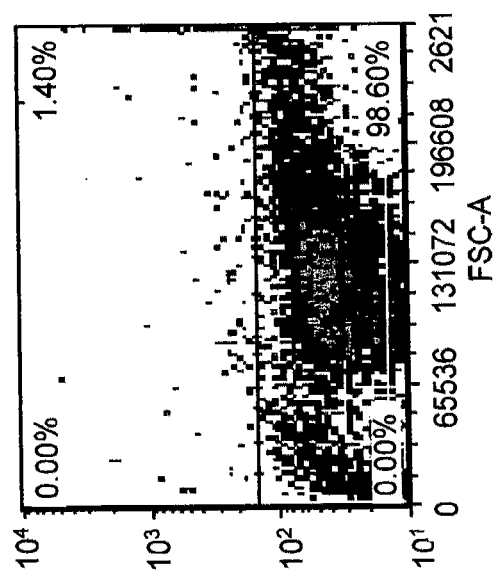

To further characterize the specific ligand bound by the invention's antibodies, the inventors first assayed the binding of the antibodies to another cell line, THP-1 (human promonocytic leukemia cell line). In order to determine whether THP-1 cells bind the antibody, cells were incubated with rat anti-peptide-6 monoclonal antibody (B24) followed by FITC staining, and then subjected to FACS analysis. Cells incubated only with the secondary antibody (FITC-goat anti-rat) served as control. As observed in FIG. 8B, this analysis revealed that 75% of the cells were bound to the B24 antibodies, whereas no binding was detected in the control cells (FIG. 8A). Having established that B24 bound THP-1 membranes, the inventors proceeded to enrich and identify the target ligand. For this purpose, hydrophilic membrane proteins, hydrophobic membrane proteins and cytoplasmic proteins were isolated from THP-1 cells, and subjected to Western blot analysis, using the B24 monoclonal anti-peptide-6 antibody (FIG. 9; lane 1—hydrophilic membrane proteins; lane 2—hydrophobic membrane proteins, lane 3—cytoplasmic proteins). Control blots were blotted with total rat immunoglobulins or medium only. As demonstrated, the B24 antibody bound three fractions of the hydrophilic membrane proteins: 52, 100 and 120 KDa. No binding was detected in the negative control blots (data not shown). These results clearly indicate that the target proteins of the anti-peptide-6 antibody are hydrophilic proteins located on the cell membrane.

Example 5

Anti-Peptide-6 Antibody Binds to the Adenylyl Cyclase Associated Protein (CAP1)

Figure 10:
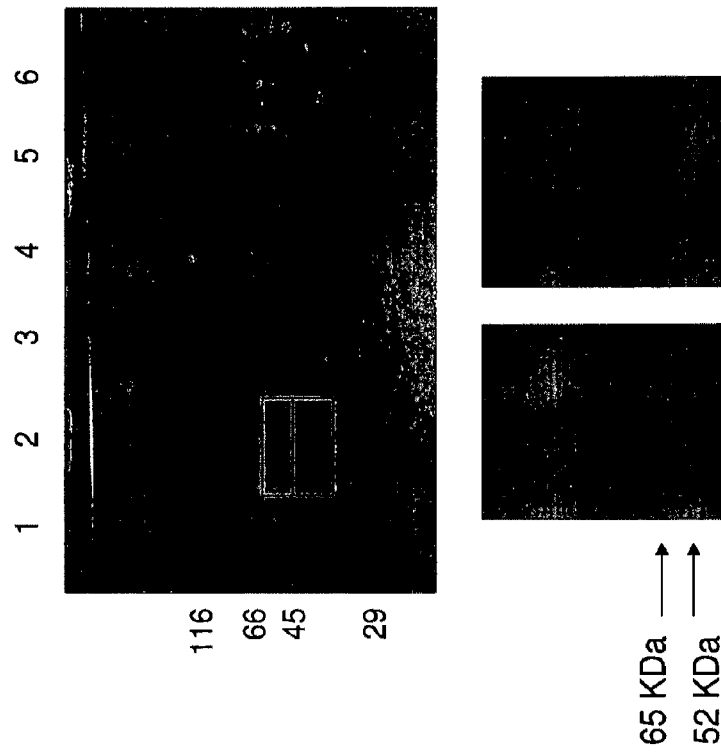

To specifically identify the target proteins of the anti-peptide-6 antibody, the hydrophilic membrane fraction of THP-1 cells was loaded on affinity columns containing anti-peptide-6 antibodies bound to Sepharose beads. The bound proteins were eluted and loaded on SDS-PAGE, followed by Coomassie Blue staining. FIG. 10 presents the Coomassie Blue staining of the anti-peptide-6 affinity chromatography eluted proteins, as can be seen in lanes 2 and 4, where lane 2 represents affinity chromatography on a rat anti-peptide-6 column and lane 4 represents affinity chromatography on a mouse anti-peptide-6 column. Two doublet bands of approximately 40 and 50 KDa were observed in both cases. Lanes 1 and 6 include the marker.

Subsequently, the bands obtained were cut out of the gel and sent for Mass Spectrometric analysis (MS) at two separate institutes. Table 1 represent sequencing results of the hydrophilic membrane proteins eluted from the rat anti-peptide-6 affinity chromatography column. As shown by the Table, MS analysis revealed that the eluted proteins included the Adenylyl Cyclase-associated Protein 1 (CAP1), a 52 KDa protein, whose amino-acid sequence is shown in FIG. 30 and denoted as SEQ ID NO.:6. This finding clearly indicates that the antibody against peptide-6 specifically binds CAP1.

TABLE 1

Sequencing Results of the Human THP-1 Hydrophilic Membrane Proteins Eluted from Rat Anti-Peptide-6 Affinity Chromatography Column

| Protein | MW | P |
|---|---|---|
| Human Histone H4 | 11400 | 5.7-6 |
| Human Histone H2B type 1B | 13900 | 3.3-6 |
| Human Histone H2B type 1J | 13900 | 9.1-8 |
| Human Histone H2B type 1A | 14200 | 7.4-8 |
| Human 60S Ribosomal protein L8 | 28000 | 7.0-4 |
| Human Actin related protein subunit 1B | 41000 | 9.6-4 |
| Human Actin, aortic smooth muscle | 42000 | 2.0-5 |
| Adenylyl-Cyclase Associated Protein | 52000 | 9.2-5 |
| Heterogenous Nuclear Ribonucleoprotein U | 90000 | 1.2-4 |

Figure 11:
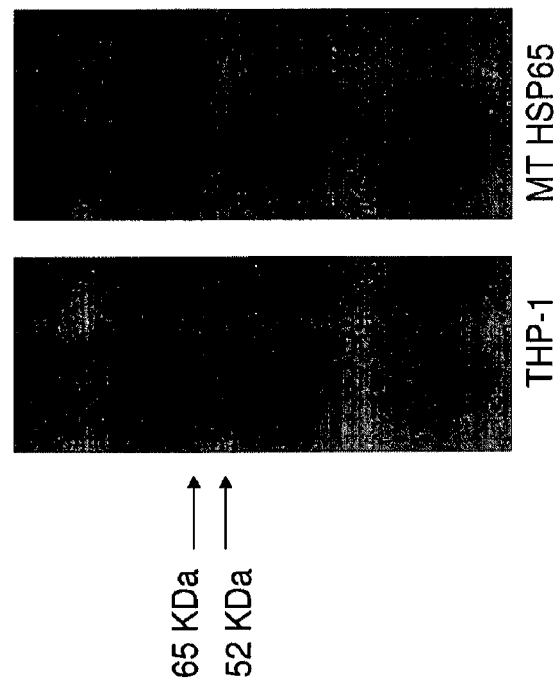

Peptide-6, the epitope used for creating the anti-peptide-6 antibody is a peptide derived from the mycobacterium tuberculosis Heat Shock Protein 65 (MT-HSP65). In order to ensure that anti-peptide-6 specifically binds to CAP1 protein and confirm the present finding, THP-1 hydrophilic membrane proteins eluted from anti-peptide-6 affinity chromatography column and MT-HSP65 were loaded on SDS-PAGE and subjected to Western blot analysis, using the rat anti-peptide-6 antibody (B24). As shown in FIG. 11, the antibody detected two different bands: a 52 KDa protein, observed in the lane loaded with the proteins obtained from the affinity column, and a 65 KDa band, compatible to the known weight of MT-HSP65. These results provide further evidence in support of an interaction between the anti-peptide-6 antibody and Adenylyl Cyclase-Associated Protein 1.

Example 6

Anti-CAP1 Antibody Binds to the Membrane of Monocytes

The finding that the anti-peptide-6 antibody binds to the CAP1 protein led the inventors to examine whether CAP1 is present on intact membranes of THP-1 promonocytes. In order to examine the possibility that CAP1 is indeed present on intact membranes of monocytes, THP-1 cells ($0.5*10^6$/tube) were incubated with anti-human CAP1 antibody (Abnova, Taiwan, 10 μg/ml), and analyzed by FACS for binding assessment. Unstained cells and FITC stained cells served as negative controls. The results shown in FIG. 12C demonstrate that about 87% of the cells were bound to the CAP1 antibody, while the negative control cells (FIGS. 12A and 12B) did not exhibit any binding.

Figure 13A:
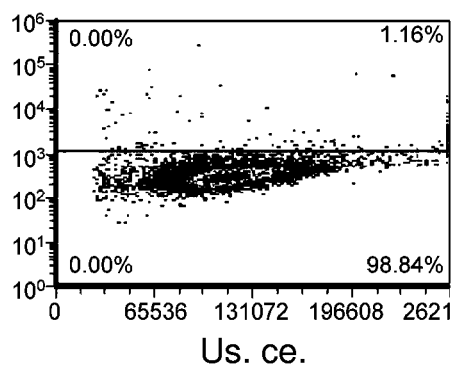
Figure 13B:
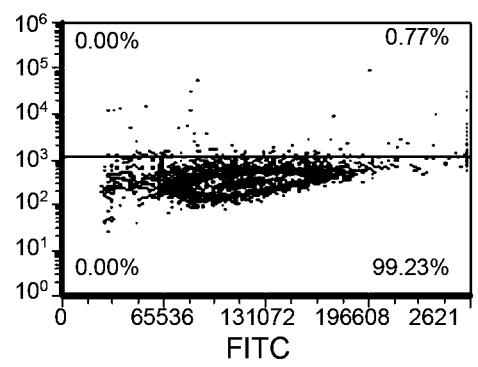
Figure 13C:
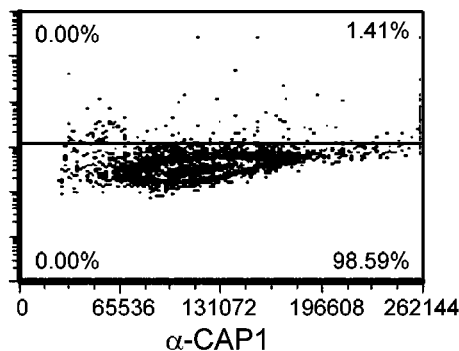

In contrast, FIG. 13C shows that intact HeLa cells, representing epithelial cells, were not bound by anti-CAP1 antibody, similar to HeLa cells incubated with secondary antibody only (FIG. 13B) or unstained (FIG. 13A).

The unique extracellular presence of CAP1 in monocytes was demonstrated by repeating the above experiment using permeabilized cells. As expected, FIG. 14 shows the binding of the anti-CAP1 antibody to permeabilized, methanol-treated THP-1 cells. As can be seen clearly in FIG. 14C, there is significant binding to the cells with the anti-CAP1 antibody (96%), while no staining shown in unstained and secondary antibody only—stained THP-1 cells (FIGS. 14A and 13B, respectively). However, in contrast with intact HeLa cells, permeabilized, methanol-treated Hela cells bound anti-CAP1 significantly (96%), as shown in FIG. 15C. Thus, permeabilized HeLa cells bind anti-CAP1 similarly to permeabilized THP-1 cells (96%) whereas the binding differs substantially in non-permeabilized, intact cells, whereby the anti-CAP1 antibody only bound to the THP-1 cells.

Thus, the extracellular presence of CAP1 is demonstrated in monocytes, but not in epithelial cells.

In order to further support the above results and confirm that binding to the membranes of monocyte cells is not a general effect of the murine-derived antibody, and as a further control, the inventors used a mouse anti-human GAPDH antibody in addition to the anti-CAP1 antibody and analyzed binding to human monocyte cells via flow cytometry. GAPDH is an internal cellular protein, present in the cytoplasm. Human THP-1 cells were stained with 1 µg of either anti-CAP1 or anti-GAPDH followed by staining with goat anti-mouse IgG FITC conjugated. As seen in FIG. 16, anti-GAPDH antibody did not bind the intact THP-1 cells (FIG. 16C), in contrast with anti-CAP1 (FIG. 16B). As expected, the permeabilization of THP-1 cells with methanol resulted in the binding of both the anti-CAP1 antibody (FIG. 17B) and the anti-GAPDH antibody (FIG. 17C).

Figure 18D:
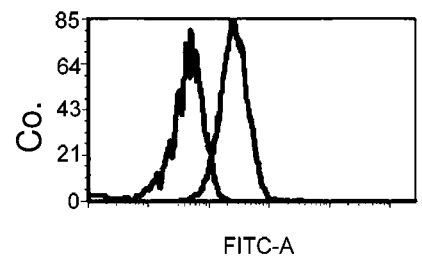

To further verify that the humanized anti-peptide-6 antibody, Proximab, binds CD14+ cells, the mouse macrophage cell line RAW 264.7 which expresses CD14+ was used. RAW cells were stained with fluorescently labeled anti-CD14-APC conjugated (FIG. 18A), or Proximab-FITC conjugated (FIG. 18B), or anti-GAPDH (FIG. 18C) or anti-CAP1 antibody (FIG. 18D), followed by staining with goat anti-mouse IgG FITC conjugated. The results demonstrate that the Proximab antibody binds a large proportion of mouse CD14+ cells (FIG. 18C), similarly to anti-CAP1 (FIG. 18D).

The experiments disclosed in this Example demonstrate unambiguously that the CAP1 protein is extracellular in THP-1 cells, and therefore supports the notion that the anti-peptide-6 antibody may bind to the cell membrane directly via interaction with the CAP1 protein.

Example 7

Anti-Peptide-6 Antibodies Bind to THP-1 Cells Via CAP1 Protein

Figure 19D:
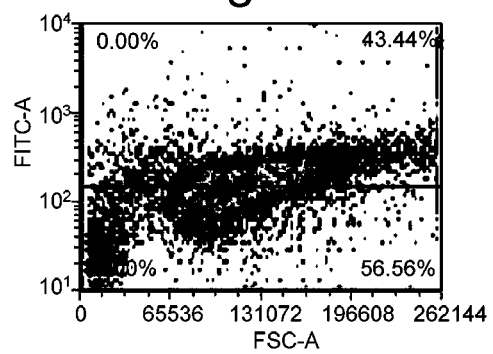

In order to verify that the anti-peptide-6 antibody recognizes monocyte membrane CAP1 and not a different cross-reactive membrane protein, the inventors applied a competition experiment, testing whether the anti-peptide-6 humanized antibody Proximab inhibits the binding of anti-CAP1 antibody to the THP-1 cells. For this purpose, THP-1 were pre-incubated with the humanized anti-peptide-6 antibody, Proximab (20 µg/ml), following by staining with anti-human CAP1 antibody (0.75 µg/ml) for one hour, and compared to cells incubated only with the anti-CAP1 antibody by FACS analysis. Unstained cells (FIG. 19A) and FITC stained cells (FIG. 19B) served as negative controls. As shown in FIG. 19D, pre-incubation with Proximab led to a significant reduction in the population of cells bound to anti-CAP1 antibody (43% binding), as compared to the cells stained with anti-CAP1 antibody alone (88% binding; FIG. 19C). As expected, no fluorescence was observed in the negative control samples (FIGS. 19A and 19B).

Taken together, these data indicate that extracellular CAP1 serves as a specific target for the anti-peptide-6 antibody, and enables its binding to monocytes.

Example 8

CAP1 Depletion Prevents Binding of the Anti-Peptide-6 Antibody to Monocytes

For further validation of these findings, showing that Proximab binds specifically to monocyte membranes via the CAP1 protein, the inventors interfered with CAP1 expression using siRNA, and evaluated the binding of Proximab to monocyte cells with reduced CAP1 expression.

In preparation for the siRNA experiments, the inventors calibrated the binding of Proximab to THP-1 cells via flow cytometry. Human THP-1 cells ($0.5*10^6$/tube) were incubated with varying concentrations of the anti-peptide-6 antibody, Proximab. Following the incubation, the cells were washed and incubated with FITC-conjugated goat anti-human Fc IgG, and analyzed for Proximab binding by flow cytometry. FIG. 20 shows the titration curve of the humanized anti-peptide-6 antibody, Proximab, binding to the THP-1 cells.

The inventors further calibrated the binding of the anti-CAP1 antibody to THP-1 cells via flow cytometry. Human THP-1 cells ($0.5*10^6$/tube) were incubated with varying concentrations of anti-CAP1 antibody. Following the incubation, the cells were washed and incubated with FITC-conjugated goat anti-mouse Fc IgG, and analyzed for anti-CAP1 antibody binding by flow cytometry. The resulting anti-CAP1 antibody titration curve is shown in FIG. 21.

Figure 22:
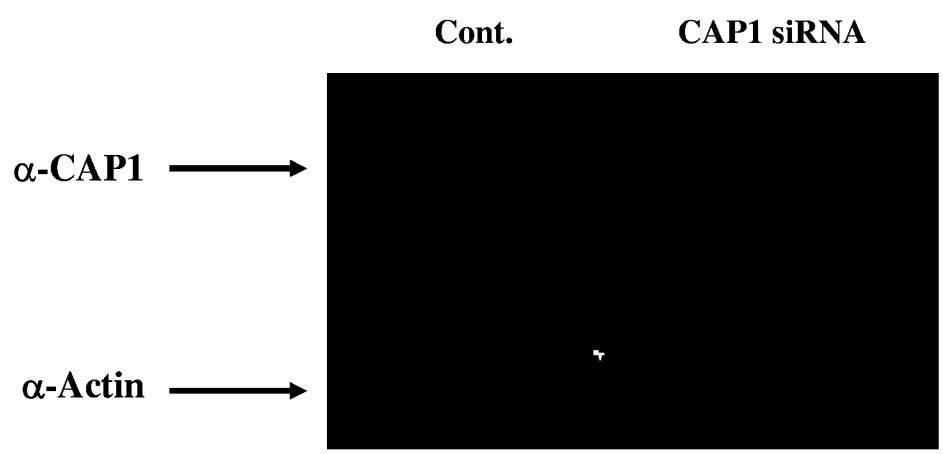

Next, the inventors analyzed the expression of CAP1, following treatment with CAP1 siRNA. Human THP-1 cells were transfected with All Star Negative siRNA or Human CAP1 siRNA (50 pmole/ml each) (Qiagen). After forty eight hours incubation, cells were harvested and then extracted using 10% SDS protein sample buffer. The proteins extract were resolved on 9% SDS-PAGE and transferred to nitrocellulose membrane by electric power. The nitrocellulose membrane was subjected to Western blotting using mouse anti-CAP1 antibody (50 ng/ml). To determine protein levels resolved on the gel, the membrane was stripped and resubjected to Western blotting using anti-alpha-actin antibody. FIG. 22 shows a specific reduction in CAP1 expression after treatment with the CAP1 siRNA.

Finally, human THP-1 cells were transfected with All Star Negative siRNA or Human CAP1 siRNA (50 pmole/ml each) and incubated with anti-CAP1 mAb (500 ng/ml) or Proximab (100 ng/ml). Flow cytometry analysis was carried out using goat anti-mouse and goat anti-human FITC conjugated antibodies. FIG. 23 shows a significant reduction in the binding of both anti-CAP1 and Proximab antibodies (FIGS. 23C and 23D, respectively) to the cells following reduction in CAP1 expression via siRNA.

The results clearly indicate that the anti-peptide-6 antibody binds monocyte membranes via CAP1.

Example 9

Mechanism of Anti-Peptide-6 Antibody Action

Figure 25:
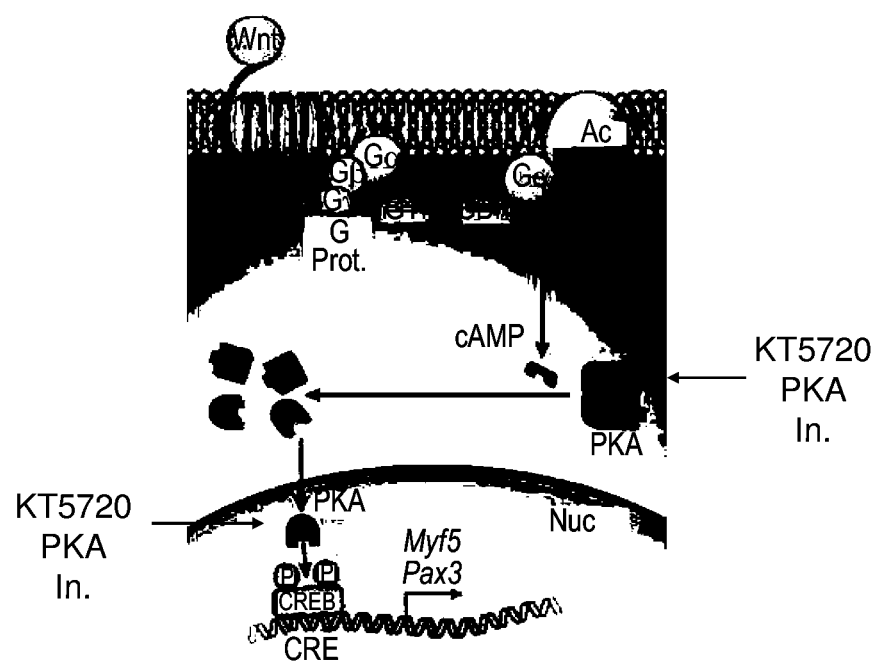
Figure 26:
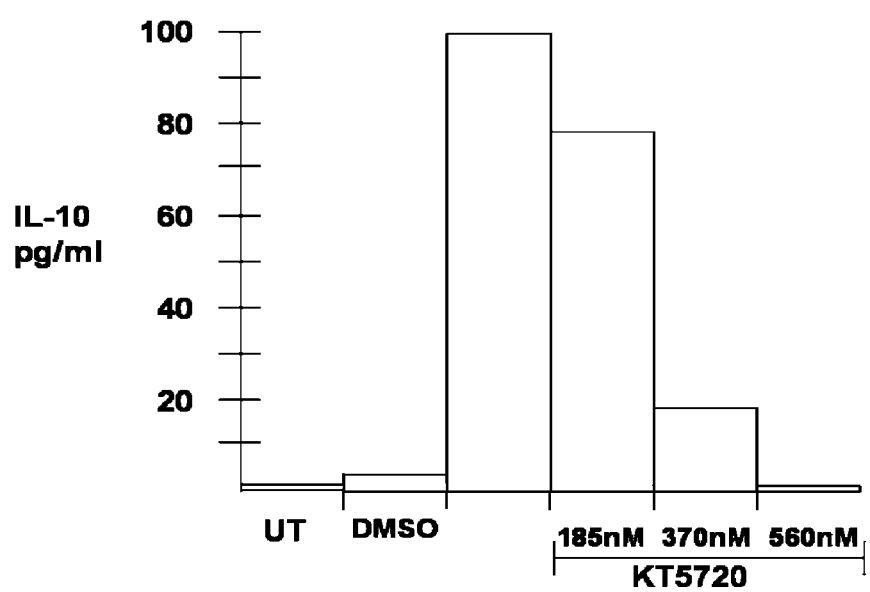

The finding that the anti-peptide-6 antibody induces up-regulation of IL-10 mRNA (see Example 1) prompted the inventors to examine the changes in protein binding to the IL-10 promoter region following exposure to anti-peptide-6 antibody. For this purpose, representative sites previously reported to enhance IL-10 transcription, namely the Sp1 [Ma, W. et al. J. Biol. Chem. 276:13664-13674 (2001)] and cAMP responsive element (CRE) [Platzer, C. et al. Eur. J. Immunol. 29:3098-3104 (1999)] binding motifs were used. Radioactively labeled oligonucleotide probes harboring these known motifs were incubated with nuclear protein extracted from PBMC cells incubated with either the rat monoclonal anti-peptide-6 antibody or with total Lewis rat IgM antibodies and then analyzed by Electro Mobility Shift Assay (EMSA). As demonstrated by FIGS. 24A and 24B, respectively, exposure of cells to B24 resulted in significant binding of CREB and SP1 transcription factors to their corresponding motifs derived from the IL-10 gene promoter, compared to treatment with total Lewis IgM, which showed only negligible protein binding. Introduction of nucleotide changes into these binding sites (mutated CRE and Sp1) abolished protein binding to both sites almost completely. These results clearly indicate that exposure of monocytes to the anti-peptide-6 antibody, stimulates the binding of transcription factors to the CRE and Sp1 motifs of the IL-10 gene promoter, thereby inducing mRNA transcription. Since CRE is typically activated through a cAMP/cAMP-dependent protein kinase A (PKA) signal transduction pathway, the inventors next examined the role of cAMP in IL-10 expression following exposure to anti-peptide-6. The following analysis took advantage of the known PKA-inhibitor, KT5720. The site of action of KT5720 [Kase, H. et al. Bioch. Biophys. Res. Com. 142:436-440 (1987)] is shown in FIG. 25. KT5720 was added in varying concentrations to the PBMCs 15 minutes prior to incubation with the anti-peptide-6 antibody. As clearly shown in FIG. 26, this intervention resulted in a dose-dependent inhibition of IL-10 secretion, proving that the PKA signal transduction pathway plays a key role in the activation of IL-10 expression by anti-peptide-6. Taken together, the data obtained leads to the conclusion that the anti-peptide-6 antibody induces IL-10 mRNA transcription by interaction with CAP1, which in turn stimulates cAMP and the activation of the PKA pathway.

Example 10

The F(ab)$_2$ Fragment of the Humanized Anti-Peptide-6 Antibody Binds to Human Monocytes and Induces IL-10 Secretion In order to further verify the specificity of the humanized anti-peptide-6 antibody binding to monocyte cells and to confirm that binding is not via the Fc receptor on these cells, the inventors generated F(ab)$_2$ fragments of the humanized anti-peptide-6 antibody (Pierce F(ab)$_2$ preparation kit), and evaluated their binding to CD14+ purified cells.

The F(ab)$_2$ fragments were labeled with FITC using Dylight™ Antibody Labeling Kit (Pierce). Human PBMC cells from a healthy donor were separated on a Ficoll gradient. The isolated cells were stained with either fluorescently labeled anti-CD14-PE conjugated (FIG. 27A) or with both humanized anti-peptide-6 antibody F(ab)$_2$ fragment (FITC conjugated) and PE-anti-CD14 (FIG. 27B). The results demonstrate significant binding of the humanized anti-peptide-6 antibody (Proximab) F(ab)$_2$ to the CD14+ cells (upper right quadrant in FIG. 27B), similar to the previous results with the full Proximab antibody. FIG. 27C depicts the percent of cells out of the CD14+ population that were stained with FITC (Without Proximab F(ab)$_2$—black, With Proximab F(ab)$_2$—grey), showing that the humanized anti-peptide-6 antibody F(ab)$_2$ binds a large percent of the CD14+ population.

The inventors next evaluated the binding of Proximab F(ab)$_2$ to CD14+ purified cells. Human PBMC cells from a healthy donor were separated on a Ficoll gradient. CD14+ cells were further isolated with anti-human CD14 magnetic beads (BD). The Proximab F(ab)$_2$ was directly labeled with FITC. The CD14+ isolated cells were stained with either anti-CD14 (APC conjugated) or with Proximab F(ab)$_2$ (FITC conjugated). Similar to previous findings with the PBMCs, the results demonstrate significant binding of Proximab F(ab)$_2$ to the CD14+ population. FIG. 27D depicts unstained cells, 27E depicts staining with F(ab)$_2$-FITC, and 27F depicts staining with anti-CD14-APC.

Example 11

Humanized Proximab F(ab)$_2$ and Anti-CAP1 Induce IL-10 Secretion

The effects of both the anti-CAP1 antibody and the Proximab F(ab)$_2$ on IL-10 secretion were also evaluated. Human PBMC cells from a healthy donor were separated on a Ficoll gradient. The isolated cells were incubated (48 h, 37° C., 7% CO$_2$) in RPMI with either Proximab (200 µg), Proximab F(ab)$_2$ (150 µg) or the anti-CAP1 antibody (8 µg), and IL-10 secretion to the medium was measured by ELISA. Untreated cells served as a control. The results in FIG. 28 show a significant increase in IL-10 secretion with Proximab F(ab)$_2$, similar to Proximab, and also with the anti-CAP1 antibody. Thus, Proximab F(ab)$_2$ binds monocyte membranes and elicits the same immune response as the intact Proximab antibody. Moreover, these results clearly indicate that CAP1 is an immunomodulatory target, and demonstrate that compounds which bind CAP1 induce an increase in expression of the anti-inflammatory cytokine IL-10, mediating said immune-modulation.

Example 12

Figure 29:
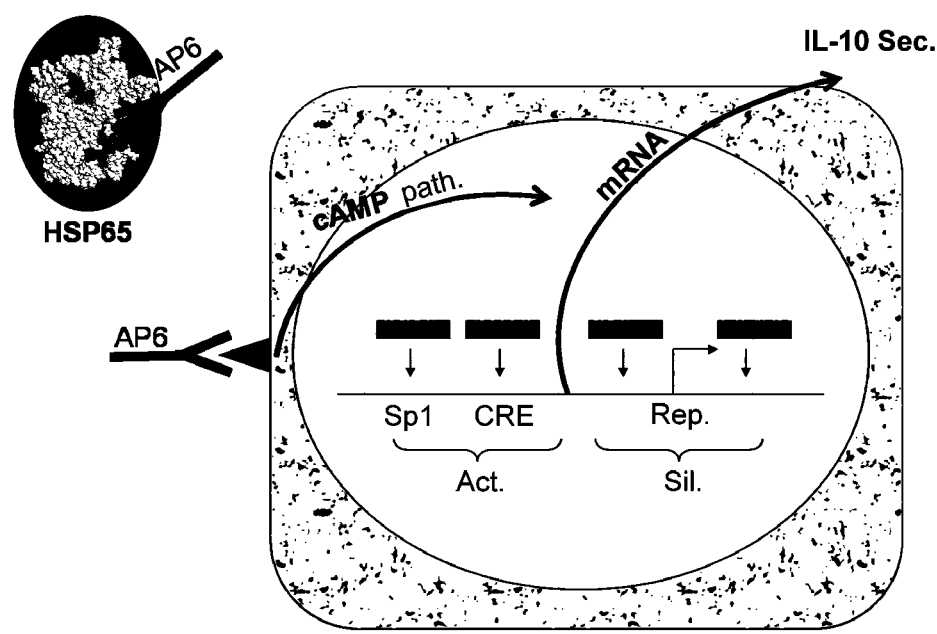

Proposed Model for Anti-Peptide-6, Anti-CAP1, Proximab and Proximab F(ab)$_2$ Action The inventors' proposed model for the action of CAP1-binding antibodies in the induction of IL-10 secretion and alleviation of inflammatory disorders is demonstrated in FIG. 29. Anti-peptide-6 as well as CAP1-binding antibodies bind an extracellular CAP1 present in CD14+ cells and activate a cAMP/PKA-dependent pathway, inducing transcription of IL-10. IL-10 secretion increases and inhibits inflammatory phenotype by tilting the Th1/Th2 balance towards Th2.

Example 13

Further Characterization of CAP1 Cellular Localization and Immuno-Modulatory Function To further investigate the immunomodulatory role of CAP1, the CAP1 protein is being expressed and purified.

Initially, CAP1 is cloned into pET22b+ vector in frame with an N terminal 6×His tag. The resulting plasmid is transformed into B121 cells, and the bacterial cells carrying the plasmid are grown and induced to express the CAP1-6×His recombinant fusion protein. The protein is then purified on a NiNta column in either native or denaturative conditions. The purified CAP1 is verified by western blot using anti CAP1 antibody. The interaction of CAP1 with humanized Proximab is studied utilizing western blot, ELISA and Biacore.

In the next step, an attempt is made to co-immuno-precipitate CAP1 with the humanized anti-peptide-6 antibody. Cell lysates are incubated with Proximab bound to magnetic beads. The proteins that bind to Proximab are then separated on SDS-PAGE and a western blot using anti-CAP1 verifies the recognition.

Finally, CAP1 to which a membrane localization signal is added is transfected in cells which the humanized anti-peptide-6 antibody does not bind, and that do not express extracellular CAP1. The cells are then incubated with either anti-CAP1 or the humanized anti-peptide-6 and analyzed by FACS, with expectation to find that cells which are so transfected are bound by both antibodies.

The invention claimed is:

1. A method for treating an immune-related disorder other than asthma in a subject in need thereof, comprising the step of administering to said subject a therapeutically effective amount of
a compound that interacts with Adenylyl Cyclase-Associated Protein (CAP1), wherein said compound is an anti-CAP1 antibody that specifically recognizes and binds CAP1, and increases IL-10, with the proviso that the antibody is not any of the polyclonal, monoclonal, chimeric or humanized anti-peptide-6 antibodies,
and wherein said subject in need is other that a subject having asthma.

2. A method for treating an immune-related disorder other than asthma in a subject in need thereof, comprising the step of administering to said subject a therapeutically effective amount of an anti-Adenylyl Cyclase-Associated Protein (CAP1) antibody that specifically recognizes and binds CAP1, or a composition comprising the same, wherein said antibody increases IL-10, thereby modulating the balance between Th1/Th2 in said subject towards the Th2 anti-inflammatory response, with the proviso that the antibody is not any of the polyclonal, monoclonal, chimeric or humanized anti-peptide-6 antibodies, and wherein said subject in need is other than a subject having asthma.

3. The method according to claim 2, wherein said immune-related disorder is arthritis, inflammatory bowel disease (IBD), diabetes or psoriasis.

4. A method for increasing the levels of IL-10 (Interleukin-10) in a subject suffering from an immune-related disorder other than asthma, comprising the step of administering to said subject a therapeutically effective amount of an anti-CAP1 antibody that specifically recognizes and binds CAP1, or a composition comprising the same, with the proviso that the antibody is not any of the polyclonal, monoclonal, chimeric or humanized anti-peptide-6 antibodies.

5. The method according to claim 4, immune-related disorder is arthritis, inflammatory bowel disease (IBD), diabetes or psoriasis.

* * * * *

SEQUENCE LISTING

<160> NUMBER OF SEQ ID NOS: 6

<210> SEQ ID NO 1
<211> LENGTH: 16
<212> TYPE: PRT
<213> ORGANISM: Mycobacterium tuberculosis

<400> SEQUENCE: 1

Gly Pro Lys Gly Arg Asn Val Val Leu Glu Lys Lys Trp Gly Ala Pro
1               5                   10                  15

<210> SEQ ID NO 2
<211> LENGTH: 20
<212> TYPE: DNA
<213> ORGANISM: Artificial
<220> FEATURE:
<223> OTHER INFORMATION: Upstream primer for IL-10

<400> SEQUENCE: 2
accaagaccc agacatcaag                                                   20

<210> SEQ ID NO 3
<211> LENGTH: 23
<212> TYPE: DNA
<213> ORGANISM: Artificial
<220> FEATURE:
<223> OTHER INFORMATION: Downstream primer for IL-10

<400> SEQUENCE: 3
gaggtacaat aaggtttctc aag                                               23

<210> SEQ ID NO 4
<211> LENGTH: 23
<212> TYPE: DNA
<213> ORGANISM: Artificial
<220> FEATURE:
<223> OTHER INFORMATION: Upstream GAPDH primer

<400> SEQUENCE: 4
cccatcacca tcttccagga gcg                                               23

<210> SEQ ID NO 5
<211> LENGTH: 23
<212> TYPE: DNA
<213> ORGANISM: Artificial
<220> FEATURE:
<223> OTHER INFORMATION: Downstream GAPDH primer

<400> SEQUENCE: 5
catgccagtg agcttcccgt tca                                               23

<210> SEQ ID NO 6
<211> LENGTH: 475
<212> TYPE: PRT
<213> ORGANISM: Homo sapiens

<400> SEQUENCE: 6

Met Ala Asp Met Gln Asn Leu Val Glu Arg Leu Glu Arg Ala Val Gly
1               5                   10                  15

Arg Leu Glu Ala Val Ser His Thr Ser Asp Met His Arg Gly Tyr Ala
                20                  25                  30

Asp Ser Pro Ser Lys Ala Gly Ala Ala Pro Tyr Val Gln Ala Phe Asp
            35                  40                  45

```
Ser Leu Leu Ala Gly Pro Val Ala Glu Tyr Leu Lys Ile Ser Lys Glu
 50                  55                  60

Ile Gly Gly Asp Val Gln Lys His Ala Glu Met Val His Thr Gly Leu
 65                  70                  75                  80

Lys Leu Glu Arg Ala Leu Leu Val Thr Ala Ser Gln Cys Gln Gln Pro
                 85                  90                  95

Ala Glu Asn Lys Leu Ser Asp Leu Leu Ala Pro Ile Ser Glu Gln Ile
            100                 105                 110

Lys Glu Val Ile Thr Phe Arg Glu Lys Asn Arg Gly Ser Lys Leu Phe
            115                 120                 125

Asn His Leu Ser Ala Val Ser Glu Ser Ile Gln Ala Leu Gly Trp Val
            130                 135                 140

Ala Met Ala Pro Lys Pro Gly Pro Tyr Val Lys Glu Met Asn Asp Ala
145                 150                 155                 160

Ala Met Phe Tyr Thr Asn Arg Val Leu Lys Glu Tyr Lys Asp Val Asp
                165                 170                 175

Lys Lys His Val Asp Trp Val Lys Ala Tyr Leu Ser Ile Trp Thr Glu
            180                 185                 190

Leu Gln Ala Tyr Ile Lys Glu Phe His Thr Thr Gly Leu Ala Trp Ser
            195                 200                 205

Lys Thr Gly Pro Val Ala Lys Glu Leu Ser Gly Leu Pro Ser Gly Pro
210                 215                 220

Ser Ala Gly Ser Gly Pro Pro Pro Pro Pro Gly Pro Pro Pro
225                 230                 235                 240

Pro Val Ser Thr Ser Gly Ser Asp Glu Ser Ala Ser Arg Ser Ala
                245                 250                 255

Leu Phe Ala Gln Ile Asn Gln Gly Glu Ser Ile Thr His Ala Leu Lys
                260                 265                 270

His Val Ser Asp Asp Met Lys Thr His Lys Asn Pro Ala Leu Lys Ala
            275                 280                 285

Gln Ser Gly Pro Val Arg Ser Gly Pro Lys Pro Phe Ser Ala Pro Lys
    290                 295                 300

Pro Gln Thr Ser Pro Ser Pro Lys Arg Ala Thr Lys Lys Glu Pro Ala
305                 310                 315                 320

Val Leu Glu Leu Glu Gly Lys Lys Trp Arg Val Glu Asn Gln Glu Asn
                325                 330                 335

Val Ser Asn Leu Val Ile Glu Asp Thr Glu Leu Lys Gln Val Ala Tyr
            340                 345                 350

Ile Tyr Lys Cys Val Asn Thr Thr Leu Gln Ile Lys Gly Lys Ile Asn
            355                 360                 365

Ser Ile Thr Val Asp Asn Cys Lys Lys Leu Gly Leu Val Phe Asp Asp
    370                 375                 380

Val Val Gly Ile Val Glu Ile Ile Asn Ser Lys Asp Val Lys Val Gln
385                 390                 395                 400

Val Met Gly Lys Val Pro Thr Ile Ser Ile Asn Lys Thr Asp Gly Cys
                405                 410                 415

His Ala Tyr Leu Ser Lys Asn Ser Leu Asp Cys Glu Ile Val Ser Ala
            420                 425                 430

Lys Ser Ser Glu Met Asn Val Leu Ile Pro Thr Glu Gly Gly Asp Phe
            435                 440                 445
```

```
Asn Glu Phe Pro Val Pro Glu Gln Phe Lys Thr Leu Trp Asn Gly Gln
    450                 455                 460

Lys Leu Val Thr Thr Val Thr Glu Ile Ala Gly
465                 470                 475
```